US012138371B2

(12) United States Patent
Sakaguchi et al.

(10) Patent No.: US 12,138,371 B2
(45) Date of Patent: Nov. 12, 2024

(54) PURIFYING METHOD, PURIFYING APPARATUS, AND PURIFYING SYSTEM

(71) Applicant: Panasonic Intellectual Property Management Co., Ltd., Osaka (JP)

(72) Inventors: Yoshihiro Sakaguchi, Hyogo (JP); Mariko Miyashita, Hyogo (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 1084 days.

(21) Appl. No.: 17/000,439

(22) Filed: Aug. 24, 2020

(65) Prior Publication Data

US 2020/0384144 A1 Dec. 10, 2020

Related U.S. Application Data

(63) Continuation of application No. PCT/JP2019/004693, filed on Feb. 8, 2019.

(30) Foreign Application Priority Data

Mar. 2, 2018 (JP) ................................ 2018-037223
Jan. 31, 2019 (JP) ................................ 2019-015622

(51) Int. Cl.
*A61L 9/14* (2006.01)
*B05B 12/12* (2006.01)

(52) U.S. Cl.
CPC .............. *A61L 9/14* (2013.01); *B05B 12/122* (2013.01); *A61L 2209/111* (2013.01)

(58) Field of Classification Search
CPC .... A61L 9/14; A61L 2209/111; B05B 12/122; B05B 12/01; G01S 17/88
See application file for complete search history.

(56) References Cited

U.S. PATENT DOCUMENTS

| | | | |
|---|---|---|---|
| 2008/0223953 | A1 | 9/2008 | Tomono et al. |
| 2014/0023556 | A1 | 1/2014 | Jiang |
| 2015/0290348 | A1 | 10/2015 | Taoka et al. |

FOREIGN PATENT DOCUMENTS

| | | | | |
|---|---|---|---|---|
| CN | 102122166 A | 7/2011 | | |
| CN | 104971374 A | 10/2015 | | |
| EP | 2929897 A1 * | 10/2015 | .............. | A61L 2/14 |
| JP | 6-237980 | 8/1994 | | |
| JP | 7-332750 | 12/1995 | | |

(Continued)

OTHER PUBLICATIONS

English translation of WO2020059442 (Year: 2020).*
International Search Report of PCT application No. PCT/JP2019/004693 dated May 14, 2019.

*Primary Examiner* — Regina M Yoo
(74) *Attorney, Agent, or Firm* — Rimon P.C.

(57) ABSTRACT

A purifying method includes determining an intended position that ejected matter ejected from an ejecting apparatus is made to reach; judging whether an object touches the ejected matter within a period of time from ejection of the ejected matter from the ejecting apparatus to reaching of the ejected matter to the intended position based on positional information on the object, the positional information being obtained by a first sensor; and controlling, based on a result of the judging, how the ejecting apparatus ejects the ejected matter into an area including the intended position.

12 Claims, 16 Drawing Sheets

(56) References Cited

FOREIGN PATENT DOCUMENTS

| | | | | | |
|---|---|---|---|---|---|
| JP | 2008-188189 | | 8/2008 | | |
| JP | 2009-014259 | | 1/2009 | | |
| JP | 2009-142528 | | 7/2009 | | |
| JP | 2016-136916 | | 8/2016 | | |
| JP | 2018-130131 | | 8/2018 | | |
| WO | 2006/095816 | | 9/2006 | | |
| WO | 2017/185138 | A1 | 11/2017 | | |
| WO | WO-2020059442 | A1 * | 3/2020 | ............... | A61L 9/14 |

* cited by examiner

138

| | WALKING SPEED |
|---|---|
| INDOOR | SPEED A |

FIG. 5

| POINT OF TIME | SENSOR A (134) | SENSOR B (134) | STATE A (136) | STATE B (136) |
|---|---|---|---|---|
| T1 | DISTANCE a | - | - | - |
| T2 | DISTANCE a | - | RESTING | - |
| T3 | DISTANCE b | DISTANCE c | MOVING | - |
| T4 | DISTANCE d | DISTANCE e | MOVING | MOVING |
| T5 | - | DISTANCE e, DISTANCE f | MOVING | RESTING |

| | WALKING SPEED |
|---|---|
| INDOOR | SPEED A |
| OUTDOOR | SPEED B |

PURIFYING METHOD, PURIFYING APPARATUS, AND PURIFYING SYSTEM

BACKGROUND

1. Technical Field

The present disclosure relates to a purifying method, a purifying apparatus, and a purifying system.

2. Description of the Related Art

For example, Japanese Unexamined Patent Application Publication No. 2008-188189 discloses a technology that utilizes a vortex ring generator to make air clean by conveying a gas or a fine liquid component to an intended place in an intended concentration.

SUMMARY

In one general aspect, the techniques disclosed here feature a purifying method including determining an intended position that ejected matter ejected from an ejecting apparatus is made to reach; judging whether an object touches the ejected matter within a period of time from ejection of the ejected matter from the ejecting apparatus to reaching of the ejected matter to the intended position based on positional information on the object, the positional information being obtained by a first sensor; and controlling, based on a result of the judging, how the ejecting apparatus ejects the ejected matter into an area including the intended position.

In one general aspect, the techniques disclosed here feature a purifying apparatus including: an ejector that ejects ejected matter; and a controller that controls the ejector. The controller determines an intended position that the ejected matter is made to reach. The controller makes a judgment on whether an object touches the ejected matter within a period of time from ejection of the ejected matter from the ejecting apparatus to reaching of the ejected matter to the intended position based on positional information on the object, the positional information being obtained by a first sensor. The controller controls, based on a result of the judgement, how the ejecting apparatus ejects the ejected matter into an area including the intended position.

In one general aspect, the techniques disclosed here feature a purifying system including the purifying apparatus according to the aforementioned aspect and the first sensor.

Further, one aspect of the present disclosure can be implemented as a program for causing a computer to execute the aforementioned purifying method. Alternatively, it may also be implemented as a computer-readable storage medium having the program stored thereon.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 5 is a diagram showing an example of positional information and movement information stored in the storage of the purifying apparatus according to Embodiment 1;

FIG. 9 is a diagram showing an example of walking information stored in a storage of a purifying apparatus according to Embodiment 2;

DETAILED DESCRIPTION

Brief Overview of the Present Disclosure

Figure 1:
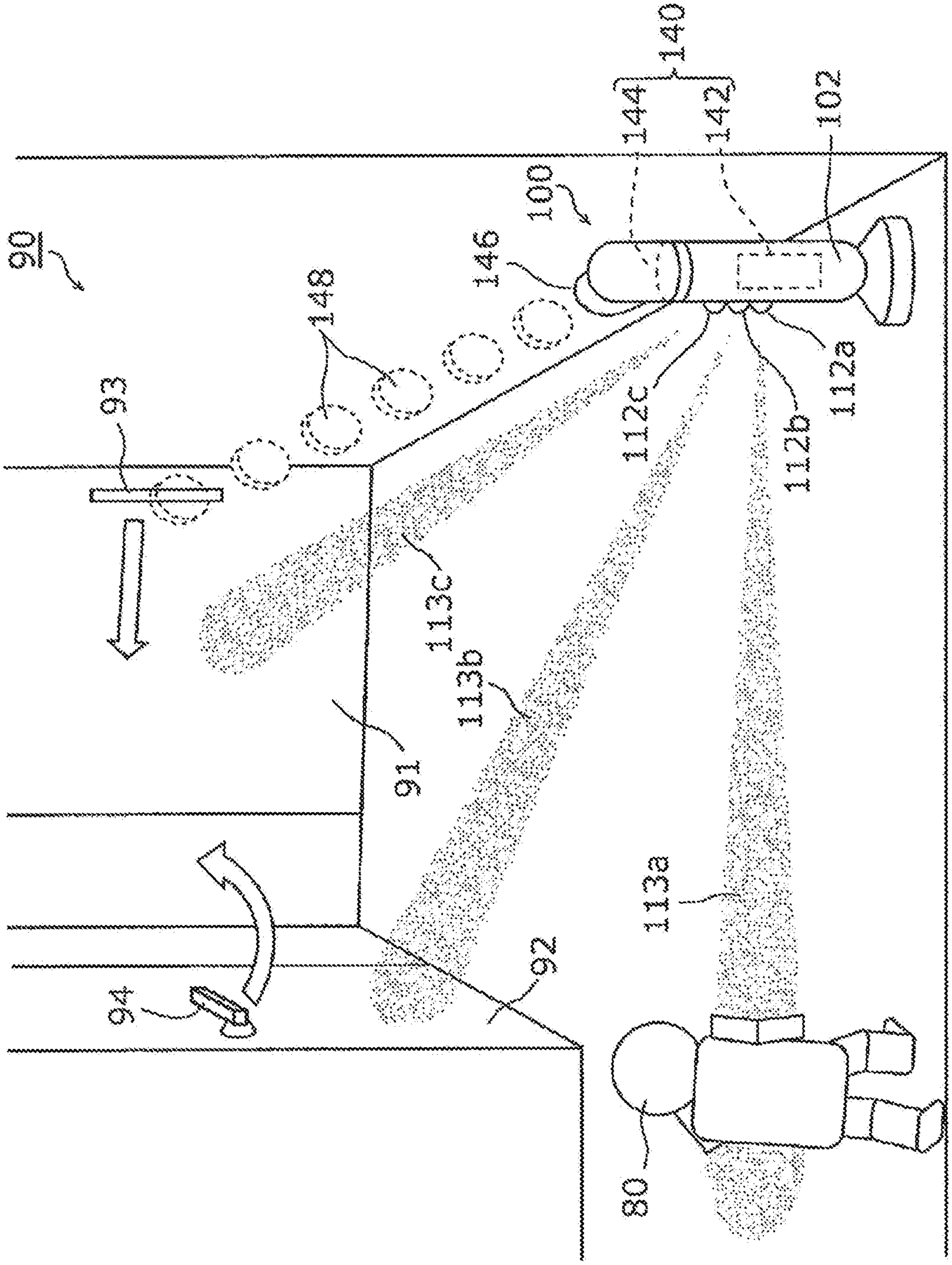
FIG. 1 is a diagram presenting an overview of a purifying system according to Embodiment 1.

First, prior to a detailed description of embodiments of the present disclosure, a brief overview of one aspect of the present disclosure is provided. The following provides a brief overview of one aspect of the present disclosure.

A purifying method according to one aspect of the present disclosure includes: determining an intended position that ejected matter ejected from an ejecting apparatus is made to reach; judging whether an object touches the ejected matter within a period of time from ejection of the ejected matter from the ejecting apparatus to reaching of the ejected matter to the intended position based on positional information on the object, the positional information being obtained by a first sensor; and controlling, based on a result of the judging, how the ejecting apparatus ejects the ejected matter into an area including the intended position.

In this way, the ejection of the ejected matter is controlled on the basis of the result of the judgment on whether the object touches the ejected matter. This makes it possible, for example, to eject the ejected matter so that the ejected matter does not touch the object and cause the ejected matter to sufficiently reach the intended position, thus making it possible to efficiently purify the intended position through the utilization of the ejected matter.

Further, for example, in a case where it has been judged in the judging that the object does not touch the ejected matter, the ejecting apparatus may be made in the controlling to eject the ejected matter into the area.

Further, for example, after it has been judged in the judging that the object does not touch the ejected matter, the ejecting apparatus may be made in the controlling to eject the ejected matter into the area.

This makes it possible, for example, to cause a sufficient amount of the ejected matter to reach the intended position, thus making it possible to efficiently purify the intended position through the utilization of the ejected matter.

Further, for example, in a case where it has been judged in the judging that the object touches the ejected matter, the ejecting apparatus may be restricted in the controlling from ejecting the ejected matter into the area so that the ejected matter does not touch the object.

Further, for example, after it has been judged in the judging that the object touches the ejected matter, the ejecting apparatus may be restricted in the controlling from ejecting the ejected matter into the area so that the ejected matter does not touch the object.

This makes it possible to reduce an amount of the ejected matter that touches the object and does not reach the intended position, thus making it possible to effectively utilize the ejected matter.

Further, for example, the ejected matter may contain an agent.

This makes it possible to render bacteria or viruses that are present in the intended positon harmless with the agent. In this way, using the agent makes it possible to efficiently purify the intended position.

Further, for example, in the determining, the intended position may be determined by using a second sensor.

This makes it possible, for example, to, by using the second sensor to sense a position in which there is a high possibility that bacteria or viruses might have developed, purify the position as the intended position. This makes it possible, for example, to determine any position in the space as the intended positon, thus making it possible to efficiently purify the interior of the space. Further, since the ejected matter can be restricted from being ejected toward a position in which bacteria or viruses have not developed, i.e, a position that is not much needed to be sanitized, the ejected matter can be effectively utilized.

Further, for example, the second sensor may be at least one selected from the group consisting of a sound sensing sensor, an infrared sensor, an imaging element, and a fluorescence detection sensor.

With this, in a case where the second sensor is at least one of a sound sensing sensor, an infrared sensor, and an imaging element, the second sensor can sense, for example, a sound or action based on a cough or sneeze of a sick person. In a case where the second sensor is a fluorescence detection sensor, the second sensor can detect fluorescence emitted by an amino acid that constitutes a bacterium or a virus.

Further, for example, the intended position may be a position in which an aerosol is present in a space in which the ejecting apparatus is disposed. Examples of the aerosol include droplets scattered by a sick person coughing or sneezing, pollen, and the like.

This makes it possible, for example, to efficiently kill bacteria or viruses contained in droplets or remove pollen.

Further, for example, in the determining, a predetermined position may be determined as the intended position.

This makes it possible to efficiently purify the intended position by prospectively determining, as the intended position, a position in which bacteria or viruses are highly likely to be present. Further, since the intended position is prospectively determined, a process for determining the intended position can be simplified. This makes it possible to achieve a simplified configuration of the purifying apparatus and a reduction in throughput.

Further, for example, the intended position may be at least a part of a door disposed in a space in which the ejecting apparatus is disposed.

This makes it possible, for example, to purify, as the intended position, a door knob that a person is highly likely to touch, thus making it possible to limit the spread of contagious infection.

Further, for example, the first sensor may be disposed in a second space separated by a door from a first space in which the ejecting apparatus is disposed. The purifying method may further include: judging, based on the positional information on the object, whether the object approaches the door within the period of time; and in a case where it has been judged that the object approaches the door, restricting the ejecting apparatus from ejecting the ejected matter.

Further, for example, the first sensor may be disposed in a second space separated by a door from a first space in which the ejecting apparatus is disposed. The purifying method may further include: judging, based on the positional information on the object, whether the object approaches the door within the period of time; and after it has been judged that the object approaches the door, restricting the ejecting apparatus from ejecting the ejected matter.

With this, for example in a case where the object is a person, there is a possibility that the door might be opened and closed when the person approaches the door. At this point in time, the opening and closing of the door generates an air current or the like, and the air current thus generated causes a change in direction of travel of the ejected matter, so that the ejected matter may no longer reach the intended position. On the other hand, the purifying method according to the present aspect restricts the ejection of the ejected matter in a case where it has been judged that the object approaches the door, thus making it possible to prevent the ejected matter from being wasted by not reaching the intended position.

Further, for example, the controlling may include waiting the ejection of the ejected matter for a first period of time or canceling the ejection of the ejected matter.

This makes it possible, for example, to after having waited for the first period of time or after having canceled the ejection once, eject the ejected matter at such a timing that the object does not touch the ejected matter. This allows a sufficient amount of the ejected matter to reach the intended position, making it possible to efficiently purify the intended position.

Further, for example, the purifying method may further include: judging whether a state of the object is a resting state or a moving state; in a case where it has been judged that the state of the object is the resting state, judging whether the resting state has been continuing for a second period of time or longer; and in a case where it has been judged that the resting state has been continuing for the second period of time or longer, outputting a signal to an external apparatus.

Further, for example, the purifying method may further include: judging whether a state of the object is a resting state or a moving state; after it has been judged that the state of the object is the resting state, judging whether the resting state has been continuing for a second period of time or longer; and after it has been judged that the resting state has been continuing for the second period of time or longer, outputting a signal to an external apparatus.

With this, since the signal is outputted to the external apparatus in a case where the object has been in the resting state for a long time, the reception of the signal by the external apparatus allows an operator, an administrator, or the like of the external apparatus to infer that an abnormality of some kind has occurred to the object. This makes it possible, for example, to notify the outside at once, for example, in a case where the object is a person and the person has suddenly fallen. In this way, the purifying method according to the present aspect can be utilized not only to purify the intended position but also to detect an abnormality in a targeted space.

Further, for example, the ejected matter may be an air current or a mist. In this case, the ejected matter does not need to contain an agent.

This makes it possible, for example, to move or dissipate bacteria or viruses by ejecting the air current to the intended position. This makes it possible to reduce the amount of bacteria or viruses that are present in the intended position, making it possible to efficiently purify the intended position.

Further, for example, the ejected matter may be an air current, and the air current may include a vortex ring formed by a gas containing an agent.

This makes it possible to, by ejecting the vortex ring, cause the agent to efficiently reach the intended position with the agent carried on the vortex ring. This makes it possible to covey a sufficient amount of the agent to the intended position, making it possible to efficiently purify the intended position.

Further, for example, a purifying apparatus according to one aspect of the present disclosure includes: an ejector that ejects ejected matter; and a controller that controls the ejector. The controller determines an intended position that the ejected matter is made to reach. The controller makes a judgment on whether an object touches the ejected matter within a period of time from ejection of the ejected matter from the ejecting apparatus to reaching of the ejected matter to the intended position based on positional information on the object, the positional information being obtained by a first sensor. The controller controls, based on a result of the judgement, how the ejecting apparatus ejects the ejected matter into an area including the intended position.

This makes it possible to efficiently purify an intended position on the basis of ejected matter as is the case with the aforementioned purifying method.

Further, for example, a purifying system according to one aspect of the present disclosure may include: the purifying apparatus according to the aspect; and the first sensor.

This makes it possible to efficiently purify an intended position on the basis of ejected matter as is the case with the aforementioned purifying method.

Further, for example, a purifying apparatus according to one aspect of the present disclosure includes: a storage in which to store positional information on an object sensed by one or more sensors; a purifier that locally ejects an agent toward an intended position; and a controller. The controller reads out the positional information from the storage in a case where a purification command has been acquired. The controller makes, on the basis of the positional information thus read out, a judgment on whether the object interferes with a path of travel of the agent within a period of time from ejection of the agent to reaching of the agent to the intended position. In a case where it has been judged that the object interferes with the path of travel, the controller restricts ejection of the agent by the purifier.

With this, in a case where it has been judged that the object interferes with the path of travel of the agent, the ejection of the agent is restricted, so that the agent can be prevented from being no longer conveyed to the intended position. Since a portion of the agent that is not conveyed to the intended position can be reduced, the agent can be efficiently used. Further, since the agent can be ejected at such a timing that the object does not interfere with the path of travel, a sufficient amount of the agent can be conveyed to the intended position, so that the intended position can be efficiently purified.

Further, for example, one of the one or more sensors may be a sensor disposed in the same space as the purifying apparatus. The controller may make, as the judgement, a first judgment on whether the object enters the path of travel within the period of time. In a case where it has been judged that the object enters the path of travel, the controller may restrict the ejection of the agent by the purifier.

With this, in a case where it has been judged that the object enters the path of travel, the ejection of the agent is restricted, so that the agent can be prevented by blocking of the path of travel by the object from being no longer conveyed to the intended position. Further, for example, even in a case where the object is a person or an animal such as a pet, the object can be prevented from impinging on the object; therefore, an agent with great purifying power can be utilized regardless of whether the agent has an influence on the health of the object. Utilizing an agent with great purifying power makes it possible to efficiently purify the intended position.

Further, for example, one of the one or more sensors may be a sensor disposed in a space separated by a door from a space in which the purifying apparatus is disposed. The controller may make, as the judgment, a second judgment on whether the object approaches the door within the period of time. In a case where it has been judged that the object approaches the door, the controller may restrict the ejection of the agent by the purifier.

For example, in a case where the object is a person, there is a possibility that the door might be opened and closed when the person approaches the door. At this point in time, the opening and closing of the door generates an air current or the like, and the air current thus generated causes the agent to deviate from the path of travel, so that the agent may no longer be conveyed to the intended position. On the other hand, the purifying method according to the present aspect restricts the ejection of the agent in a case where it has been judged that the object approaches the door, thus making it possible to prevent the agent from being no longer conveyed to the intended position.

Further, for example, the intended position may be at least a part of the door.

With this, in a case where the door is opened and closed, the intended position per se moves. The purifying method according to the present aspect restricts the ejection of the agent in a case where it has been judged that the object approaches the door, thus making it possible to prevent the agent from being no longer conveyed to the intended position.

Further, for example, in a case where it has been judged that the object interferes with the path of travel, the controller may wait the ejection of the agent by the purifier for a predetermined period of time or cancel the ejection of the agent by the purifier.

This makes it possible, for example, to after having waited for the predetermined period of time or after having canceled the ejection once, eject the agent at such a timing that the object does not interfere with the path of travel. This makes it possible to convey a sufficient amount of the agent to the intended position, making it possible to efficiently purify the intended position.

Further, for example, the purifying apparatus according to the aspect of the present disclosure may further include a communicator that performs communication with an external apparatus. The controller may further judge whether a state of the object is a resting state or a moving state. In a case where the resting state has been continuing for a predetermined period of time or longer, the controller may output a predetermined signal to the external apparatus via the communicator.

With this, since the signal is outputted to the external apparatus in a case where the object has been in the resting state for a long time, the reception of the signal by the external apparatus allows an operator, an administrator, or the like of the external apparatus to infer that an abnormality of some kind has occurred to the object. This makes it possible, for example, to notify the outside at once, for example, in a case where the object is a person and the person has suddenly fallen. In this way, the purifying apparatus according to the present aspect can be utilized not only to purify the intended position but also to detect an abnormality in a targeted space.

Further, for example, the purifier may eject, toward the intended position, a vortex ring formed by a gas containing the agent.

This makes it possible to, by ejecting the vortex ring, cause the agent to efficiently reach the intended position with the agent carried on the vortex ring. This makes it possible to convey a sufficient amount of the agent to the intended position, making it possible to efficiently purify the intended position.

Further, for example, a purifying system according to one aspect of the present disclosure includes: the purifying apparatus; and the one or more sensors.

This makes it possible to efficiently purify an intended position as is the case with the aforementioned purifying apparatus.

Further, a purifying method according to one aspect of the present disclosure is a purifying method for locally ejecting an agent toward an intended position, the purifying method including: storing, in a storage, positional information on an object sensed by one or more sensors; reading out the positional information from the storage in a case where a purification command has been acquired; making, on the basis of the positional information thus read out, a judgment on whether the object interferes with a path of travel of the agent within a period of time from ejection of the agent to reaching of the agent to the intended position; and in a case where it has been judged that the object interferes with the path of travel, restricting ejection of the agent by the purifier.

This makes it possible to efficiently purify an intended position as is the case with the aforementioned purifying apparatus.

In the present disclosure, all or a part of any of circuit, unit, device, part or portion, or any of functional blocks in the block diagrams may be implemented as one or more of electronic circuits including, but not limited to, a semiconductor device, a semiconductor integrated circuit (IC) or an LSI. The LSI or IC can be integrated into one chip, or also can be a combination of plural chips. For example, functional blocks other than a memory may be integrated into one chip. The name used here is LSI or IC, but it may also be called system LSI, VLSI (very large scale integration), or ULSI (ultra large scale integration) depending on the degree of integration. A Field Programmable Gate Array (FPGA) that can be programmed after manufacturing an LSI or a reconfigurable logic device that allows reconfiguration of the connection or setup of circuit cells inside the LSI can be used for the same purpose.

Further, it is also possible that all or a part of the functions or operations of the circuit, unit, device, part or portion are implemented by executing software. In such a case, the software is recorded on one or more non-transitory recording media such as a ROM, an optical disk or a hard disk drive, and when the software is executed by a processor, the software causes the processor together with peripheral devices to execute the functions specified in the software. A system or apparatus may include such one or more non-transitory recording media on which the software is recorded and a processor together with necessary hardware devices such as an interface.

The following describes embodiments in concrete terms with reference to the drawings.

It should be noted that the embodiments to be described below illustrate general or specific examples. The numerical values, shapes, materials, constituent elements, locations of placement and forms of connection of constituent elements, steps, and orders of steps that are shown in the following embodiments are mere examples and are not intended to limit the present disclosure. Further, those of the constituent elements according to the following embodiments which are not recited in an independent claim are described as optional constituent elements.

Further, the drawings are schematic views and are not necessarily strict illustrations. Accordingly, for example, the drawings are not necessarily to scale. Further, the drawings assign identical signs to substantially identical components and omit or simplify repeated descriptions.

Embodiment 1

Brief Overview

First, a brief overview of a purifying system according to Embodiment 1 is provided with reference to FIG. 1. FIG. 1 is a diagram presenting an overview of a purifying system 100 according to the present embodiment.

The purifying system 100 is a system that purifies a predetermined place in a predetermined space such as the interior of a room with an agent ejected by a purifying apparatus 102, FIG. 1 illustrates a space 90 including a place to be purified by the purifying apparatus 102.

The space 90 is for example a room of a building such as a nursing home or a hospital. Examples of the space 90 include, but are not limited to, an enclosed space such as a space segmented by a wall, a window, a door, a floor, a ceiling, and the like. The space 90 may be an outdoor open space. Alternatively, the space 90 may be an interior space of a movable body such as a bus or an airplane.

As shown in FIG. 1, the space 90 is provided with a door 91 and a door 92. The door 91 and the door 92 can both be freely opened and closed from inside and outside the space 90.

The door 91 is a sliding door and is provided with a handle 93. The handle 93 is for example a member having the shape of a long and thin rod that a person 80 can easily grasp, and is fixed to a surface of a door panel of the door 91. Alternatively, the handle 93 may be a depression that is lower than the door panel of the door 91 to such an extent that the person 80 can insert his/her finger into the depression.

The person 80 can open and close the door 91 by sliding the door 91 sideways with his/her hand put on the handle 93. In FIG. 1, the straight arrow outline with a blank inside illustrated near the handle 93 indicates the direction in which the door 91 is opened. The handle 93 is not limited to a particular shape or attachment position.

The door 92 is a hinged door and is provided with a door knob 94. The door knob 94 is at least partly rotatable. The person 80 can open and close the door 92 by turning the door knob 94 and pulling it toward him/her or pushing it out away from him/her. In FIG. 1, the straight arrow outline with a blank inside illustrated near the door knob 94 indicates the direction in which the door 92 is opened. The door knob 94 is not limited to a particular shape or attachment position.

In the present embodiment, the handle 93 and the door knob 94 are intended positions to be purified. That is, the handle 93 and the door knob 94 are positions that ejected matter should be made to reach. Specifically, the handle 93 and the door knob 94 are positions that the agent ejected by the purifying apparatus 102 should be made to reach.

The handle 93 and the door knob 94 are parts that many people touch normally in opening and closing the doors. For this reason, adhesion of pathogens such as viruses or bacteria to the handle 93 and the door knob 94 leads to spread of infection of a disease. To address this problem, the purifying system 100 according to the present embodiment makes the handle 93 and the door knob 94 intended positions to be purified.

Intended positions are not limited to parts of the doors such as the handle 93 and the door knob 94. Other examples of intended positions may include a terminal for operating a domestic appliance that is present in the space 90, a trace of wiping out of vomit of the person 80, or the like.

In the present embodiment, the purifying apparatus 102 is disposed in the space 90. The purifying apparatus 102 does not need to be entirely disposed in the interior of the space 90 but may for example have only its agent ejection port 146 located in the space 90. The purifying apparatus 102 may for example be fixed in a predetermined position in the space 90.

The purifying apparatus 102 is an example of an ejecting apparatus that ejects ejected matter. The ejected matter is for example an air current and contains the agent. Specifically, the purifying apparatus 102 is an apparatus that locally ejects the agent toward an intended position. Locally ejecting the agent makes it possible to prevent the agent from pervading an area that does not need purification, thereby making it possible to less waste the agent.

The term "locally ejecting" here means ejecting the agent only into a predetermined area centered at a predetermined direction of ejection instead of sprinkling the agent so that the agent is scattered all over the space 90. That is, the direction of ejection of the agent has directivity. For example, an area of reach of the agent in an intended position ranges from several centimeters to 100 cm in diameter. For example, the range of diameters may be from 5 cm to 100 cm.

A path of travel of the agent is a portion through which the agent passes from the agent ejection port 146 of the purifying apparatus 102 to an intended position. Examples of length of the path of travel include, but are not limited to, not shorter than several centimeters and not longer than and several tens of centimeters.

In the present embodiment, the purifying apparatus 102 ejects, toward an intended position, vortex rings 148 formed by a gas containing the agent. That is, the agent is conveyed to the intended position in such a manner as to fly in the air. For this reason, the path of travel of the agent is a path of flight of the agent formed in the air.

The agent is a liquid for making microorganisms such as viruses or bacteria harmless by purification. Specifically, the agent is an aqueous hypochlorous acid, a sodium hypochlorite formulation, an alcohol formulation, or the like. The agent does not need to be a liquid but may be a gas or a solid.

As shown in FIG. 1, the person 80 is present in the space 90, and the person 80 can freely walk around in the space 90. The person 80 is an example of a movable object and is an object that may touch the ejected matter. Specifically, the person 80 is an object that may interfere with the path of travel of the agent. The object is not limited to a person but may be an animal such as a pet. Alternatively, the object does not need to be a living organism but may be a cleaning robot or the like.

Since the person 80 freely moves in the space 90, the person 80 may enter the path of travel of the agent. In a case where the person 80 has entered the path of travel of the agent, an amount of the agent that is needed for purification may no longer reach the intended position. Further, since the person 80 may be exposed to the agent, use of a type of agent that has an influence on the health of the person 80 is not allowed.

Even in a space in which the person 80 is present, the purifying system 100 according to the present embodiment conveys an agent to an intended position located away from the purifying apparatus 102 and purifies the intended position with the agent thus conveyed.

Configuration

Next, a configuration of the purifying system 100 according to the present embodiment is described with reference to FIG. 2.

Figure 2:
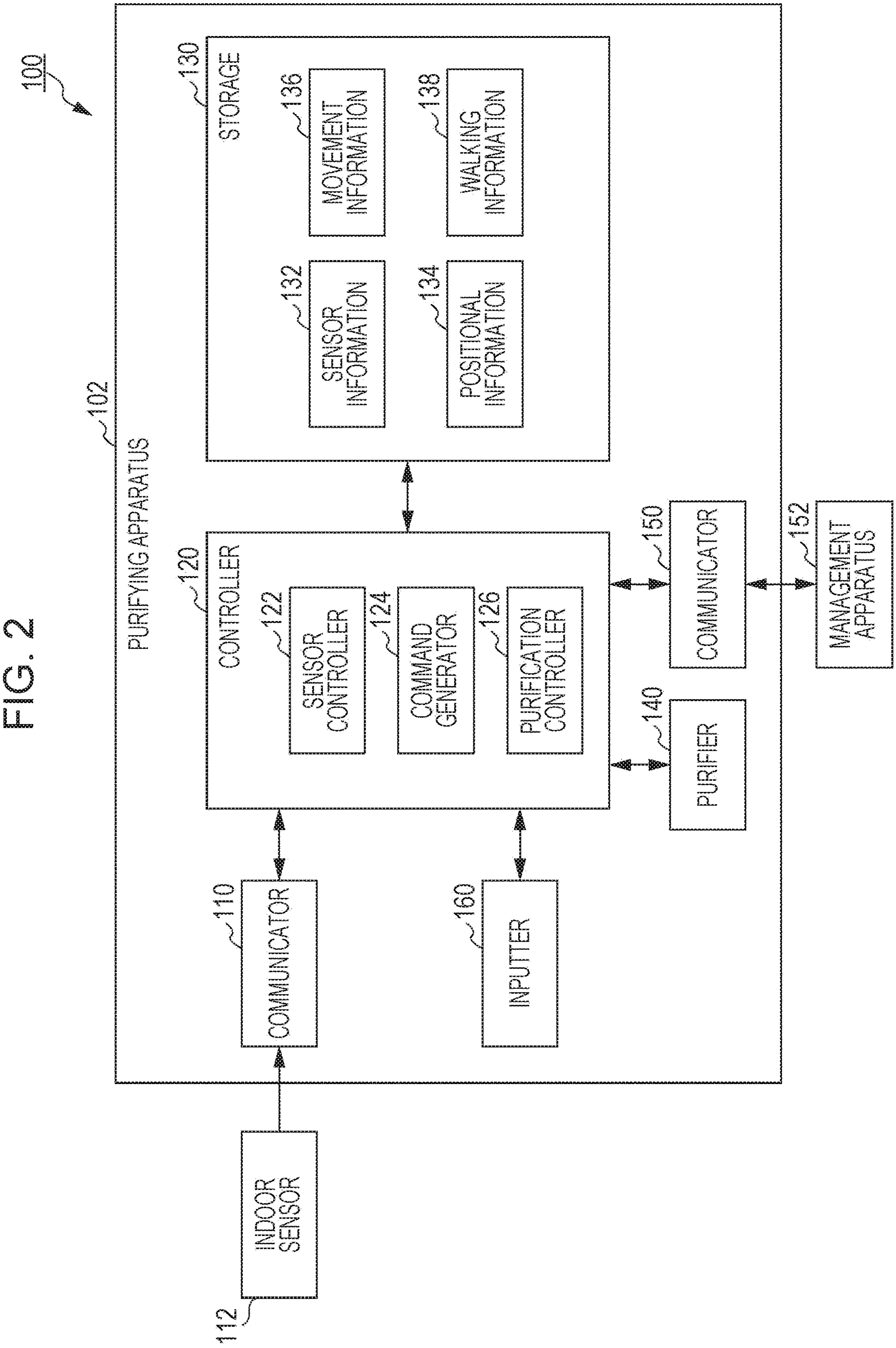
FIG. 2 is a block diagram showing a configuration of the purifying system according to Embodiment 1.

FIG. 2 is a block diagram showing a configuration of the purifying system 100 according to the present embodiment. As shown in FIG. 2, the purifying system 100 includes the purifying apparatus 102, one or more indoor sensors 112, and a management apparatus 152.

The one or more indoor sensors 112 are each an example of a first sensor and, for example, are disposed in the same space as the purifying apparatus 102. The one or more indoor sensors 112 are human sensors that detect the position of the person 80.

FIG. 1 illustrates three indoor sensors 112*a*, 112*b*, and 112*c* as the one or more indoor sensors 112. The three indoor sensors 112*a*, 112*b*, and 112*c* each have the same configuration. In the following description, the three indoor sensors 112*a*, 112*b*, and 112*c* are collectively referred to as "indoor sensors 112" in a case where no particular distinction is made among the three indoor sensors 112*a*, 112*b*, and 112*c*. The number of indoor sensors 112 that the purifying system 100 includes may be 1 or 2 or not smaller than 4.

Each of the indoor sensors 112 is for example an infrared sensor having a predetermined sensing region. The indoor sensor 112 outputs a sensing signal upon entry of the person 80 into the sensing region. The sensing signal is acquired by a controller 120 of the purifying apparatus 102 via a communicator 110 of the purifying apparatus 102.

In FIG. 1 the three indoor sensors 112*a*, 112*b*, and 112*c* have their respective sensing regions 113*a*, 113*b*, and 113*c* indicated by half-tone dot meshing. The sensing regions 113*a*, 113*b*, and 113*c* are different from one another. The sensing regions 113*a*, 113*b*, and 113*c* may partly overlap.

The sensing region 113 is formed in a position most distant of the plurality of sensing regions from the path of travel of the agent in the space 90, specifically the path of flight of the vortex rings 148, The sensing region 113*c* is formed in a position nearest of the plurality of sensing regions to the path of flight of the vortex rings 148. The sensing region 113*b* is formed between the sensing region 113*a* and the sensing region 113*c*.

In the present embodiment, each indoor sensor 112 is assigned a unique identifier for identification of the plurality of indoor sensors 112. A sensing signal contains an identifier that is unique to an indoor sensor that outputs the sensing signal. This allows the purifying apparatus 102 to identify, on the basis of an identifier contained in a sensing signal, an indoor sensor 112 from which the sensing signal was transmitted.

For example, assume a case where the person 80 walks toward the door 91 from the position shown in FIG. 1. At this point in time, a sensing signal is outputted from the indoor sensor 112*a*, as the person 80 enters the sensing region 113*a* first, Next, a sensing signal is outputted from the indoor sensor 112*b*, as the person 80 enters the sensing region 113*b*. Finally, a sensing signal is outputted from the indoor sensor 112*c*, as the person 80 enters the sensing region 113*c*.

At this point in time, the purifying apparatus 102, which has received the sensing signals in sequence, finds that the order of the sensing signals thus received is the order of the indoor sensor 112*a*, the indoor sensor 112*b*, and the indoor sensor 112*c*. This allows the purifying apparatus 102 to calculate the moving direction of the person 80. Further, the moving speed of the person 80 can be calculated on the basis of the points of time at which the sensing signals were received.

Further, each of the indoor sensors 112*a*, 112*b*, and 112*c* acquires a distance to the person 80 in its sensing region and outputs a sensing signal containing distance information indicating the distance thus acquired. This allows the purifying apparatus 102 to calculate the moving direction and moving speed of the person 80 in more detail. This makes it possible to judge with a higher degree of accuracy whether the person 80 interferes with the path of travel of the agent. Each of the indoor sensors 112*a*, 112*b*, and 112*c* does not need to be able to acquire a distance to the person 80 but may judge only the presence or absence of the person 80 in its sensing region.

The indoor sensors 112 do not need to be infrared sensors. For example, the indoor sensors 112 may be image sensors that generate still images or moving images by taking photos in the space 90. The position of the person 80 can be identified by analyzing the images obtained by the image sensors. Alternatively, the indoor sensors 112 may be ranging sensors such as TOF (time-of-flight) sensors. For example, the indoor sensors 112 may be LIDAR (laser imaging detection and ranging) sensors.

As shown in FIG. 1, the three indoor sensors 112*a*, 112*b*, and 112*c* are integrated with the purifying apparatus 102. Alternatively, at least one of the three indoor sensors 112*a*, 112*b*, and 112*c* may be provided as a separate entity from the purifying apparatus 102. For example, at least one of the three indoor sensors 112*a*, 112*b*, and 112*c* may be provided on a ceiling, a wall, or the like that constitutes the space 90. The three indoor sensors 112*a*, 112*b*, and 112*c* output sensing signals to the purifying apparatus 102 by communicating with the communicator 110 of the purifying apparatus 102.

As shown in FIG. 2, the purifying apparatus 102 includes the communicator 110, the controller 120, a storage 130, a purifier 140, a communicator 150, and an inputter 160.

The communicator 110 performs communication with each of the plurality of indoor sensors 112 by cable or by radio. For example, the communicator 110 performs wireless communication conforming to a wireless communication standard such as Wi-Fi (registered trademark), Bluetooth (registered trademark), or ZigBee (registered trademark). The communicator 110 acquires a sensing signal from each of the plurality of indoor sensors 112. The sensing signals thus acquired are outputted to a sensor controller 122 of the controller 120.

As shown in FIG. 2, the controller 120 includes the sensor controller 122, a command generator 124, and a purification controller 126. The controller 120 is achieved, for example, by a nonvolatile memory in which a program is stored, a volatile memory serving as a transitory recording region in which to execute the program, an I/O port, a processor that executes the program, or other components. The sensor controller 122, command generators 124, and purification controller 126 of the controller 120 may each be implemented as software that is executed by the processor or may each be implemented as hardware such as an electronic circuit including a plurality of circuit elements.

The sensor controller 122 controls an operation involving the indoor sensors 112. Specifically, the sensor controller 122 generates positional information 134 on the person 80 on the basis of sensing signals outputted from the indoor sensors 112 and stores the positional information 134 in the storage 130.

Specifically, upon receiving a sensing signal from an indoor sensor 112 via the communicator 110, the sensor controller 122 compares an identifier contained in the sensing signal with sensor information 132 stored in the storage 130 and thereby identifies the indoor sensor 122 from which the sensing signal was transmitted. For each indoor sensor 112 identified, the sensor controller 122 generates positional information 134 on the person 80 on the basis of the distance information contained in the sensing signal.

The sensor controller 122 stores the positional information 134 in the storage 130 in association with a point of time of sensing. The point of time of sensing is for example a point of time at which the communicator 110 acquired the sensing signal. Alternatively, in a case where the sensing signal contains time information indicating a point of time at which the person 80 was sensed, the point of time of sensing may be a point of time indicated the time information contained in the sensing signal.

In the present embodiment, the sensor controller 122 further judges the state of the person 80 on the basis of a sensing signal. Specifically, the sensor controller 122 judges whether the state of the person 80 is a moving state in which the person 80 is moving or a resting state in which the person 80 is not moving. For example, the sensor controller 122 judges the state of the person 80 by judging the presence or absence of a change in position of the person 80 as indicated by two pieces of positional information 134 associated with two consecutive points of time. In the presence of a change in position of the person 80, the sensor controller 122 judges that the state of the person 80 is a moving state. In the absence of a change in position of the person 80, the sensor controller 112 judges that the state of the person 80 is a resting state. The sensor controller 122 stores, in the storage 130, movement information indicating a judgment result.

Further, the sensor controller 122 outputs a predetermined signal to the management apparatus 152 via the communicator 150 in a case where a resting state has been continuing for a predetermined period of time. In a case where the person 80 has been in a resting state for a long time, there is a possibility that an abnormality of some kind might have occurred to the person 80, e.g, that the person 80 might have suddenly fallen. To address this problem, the sensor controller 122 can output a signal to the management apparatus 152 via the communicator 150 and thereby notify the management apparatus 152 of a possible abnormality in the space 90 in which the purifying apparatus 102 is installed. Examples of the signal that the sensor controller 122 outputs include, but are not limited to, a signals for making a warning sound or a warning display. Further, instead of being outputted to the management apparatus 152, the signal may be outputted, for example, to a speaker disposed outside the space 90 or a light-emitting apparatus such as a red lamp.

The command generator 124 generates a purification command and outputs the purification command thus generated to the purification controller 126. The purification command is a command to purify an intended position. The purification command contains information indicating the intended position. The purification command may contain control parameters regarding the intensity of purification. Examples of the control parameters include the concentration of the agent, the number of times a vortex ring 148 is ejected, the air volume of a vortex ring 148, and the like.

The command generator 124 generates a purification command, for example, on the basis of predetermined schedule information. The schedule information is information that indicates a timing of purification of the intended position, i.e. a timing of ejection of the ejected matter. Specifically, the schedule information is information that indicates a timing of ejection of the agent. For example, the schedule information indicates time intervals, such as 30 minutes or 1 hour, of ejection of the agent ora point of time, such as 10:00 or 10:30, of ejection of the agent.

Alternatively, the command generator 124 may generate a purification command on the basis of a user operation accepted by the inputter 160. This makes it possible to purify the intended position at any timing that the user desires.

Further, the command generator 124 may generate a purification command on the basis of an instruction acquired via the management apparatus 152 and the communicator 150. This makes it possible, for example, to purify the intended position at any timing that an administrator or user of the management apparatus 152 desires.

The purification controller 126 controls the purifier 140. Specifically, the purification controller 126 determines an intended position that the ejected matter is made to reach. The purification controller 126 judges, on the basis of positional information on the person 80 as acquired by an indoor sensor 112, whether the person 80 touches the ejected matter within a period of time from ejection of the ejected matter from the purifier 140 to reaching of the ejected matter to the intended position. The purification controller 126 controls, on the basis of a result of the judgment, how the purifier 140 ejects the ejected matter into an area including the intended position. More specifically, the purification controller 126 reads out positional information 134 from the storage 130 in a case where a purification command has been acquired. The purification controller 126 judges, on the basis of the positional information 134 thus read out, whether the person 80 interferes with the path of travel of the agent in a period of time (hereinafter referred to as "required period of time") from ejection of the agent to reaching of the agent to the intended position, i.e. the likelihood of interference.

The required period of time is a period of time from ejection of a vortex ring 148 from the purifying apparatus 102 to reaching of the vortex ring 148 thus ejected to the intended position. In a case where a plurality of vortex rings 148 are ejected upon one purification command, the required period of time is a period of time from ejection of the first vortex ring 148 to reaching of the last vortex ring 148 to the intended position. For example, the purification controller 126 calculates the required period of time on the basis of the distance between the intended position and the purifying apparatus 102, the velocity of ejection of a vortex ring 148, the duration of ejection of vortex rings 148, and the number of times a vortex ring 148 is ejected, and the like.

The path of travel of the agent is equivalent to the path of flight of the vortex rings 148. Since, in a normal case, a vortex ring 148 travels in a straight line, the path of travel of the agent falls within a circular columnar area centered on a straight line connecting the ejection port 146, through which the vortex ring 148 is ejected, of the purifying apparatus 102 with the intended position. The diameter of the area is equivalent to the outer diameter of the vortex ring 148. In the case of a change in direction of travel of a vortex ring 148 by an air current or the like, the path of travel may be curved in conformance with a motion of the vortex ring 148.

In the present embodiment, the term "interference" means entry of the person 80 into the path of travel. Specifically, the purification controller 126 judges the likelihood of interference by judging whether the person 80 enters the path of travel of the agent within the required period of time, i.e. by judging the likelihood of entry. For example, the purification controller 126 reads out positional information 134, movement information 136, and walking information 138 from the storage 130 and determines the likelihood of entry on the basis of the information 134, movement information 136, and walking information 138 thus read out.

In a case where the purification controller 126 has judged that the person 80 touches the ejected matter, the purification controller 126 restricts the ejection of the ejected matter by the purifier 140 so that the person 80 does not touch the ejected matter. For example, in a case where the purification controller 126 has judged that the person 80 interferes with the path of travel of the agent, the purification controller 126 restricts the ejection of the agent by the purifier 140. In the present embodiment, in a case where the purification controller 126 has judged that the person 80 enters the path of travel of the agent, the purification controller 126 restricts the ejection of the agent by the purifier 140.

The restriction of ejection is for example waiting or canceling the ejection. That is, in a case where the purification controller 126 has judged that the person 80 interferes with the path of travel of the agent, the purification controller 126 waits the ejection of the agent by the purifier 140 for a predetermined period of time or cancels the ejection of the agent by the purifier 140.

A period of time for which to wait the ejection (hereinafter referred to as "waiting period") is for example not shorter than several seconds and not longer than several minutes. After waiting, the purification controller 126 judges again whether the person 80 interferes with the path of travel of the agent.

The purification controller 126 cancels the ejection when the agent cannot be ejected, for example, in a case where the purification controller 126 has repeated a judgment of the likelihood of interference a predetermined number of times or a predetermined period of time has elapsed since the purification controller 126 received a purification command. In a case where the purification controller 126 has canceled the ejection, the purification controller 126 is in a waiting state until a next purification command is acquired. In a case where the purification controller 126 has judged that the person 80 interferes with the path of travel, the purification controller 126 may cancel the ejection immediately without waiting the ejection once.

In a case where the purification cantroller 126 has judged that the person 80 does not touch the ejected matter, the purification controller 126 causes the purifier 140 to eject the ejected matter. For example, in a case where the purification controller 126 has judged that the person 80 does not interfere with the path of travel of the agent, the purification controller 126 causes the purifier 140 to eject the agent by ejecting a vortex ring 148. For example, the purification controller 126 sets conditions such as the concentration of the agent, the number of time a vortex ring 148 is ejected, and the air volume of a vortex ring 148 on the basis of the control parameters contained in a purification command. The purifier 140 ejects, on the basis of the conditions thus set, a vortex ring 148 containing the agent.

The storage 130 is for example a nonvolatile storage device such as a semiconductor memory or an HDD (hard disk drive). As shown in FIG. 2, the storage 130 has stored therein sensor information 132, positional information 134, movement information 136, and walking information 138.

The sensor information 132 indicates an association between the respective identifiers of the plurality of indoor sensors 112 connected to the purifying apparats 102 by cable or by radio and the positions of the sensing regions. The sensor information 132 is updated in a case where an indoor sensor 112 has been newly added and a case where the sensing region of an existing indoor sensor 112 has been changed.

The positional information 134 is information that indicates the position of the person 80 sensed by an indoor sensor 112. The positional information 134 is associated with a point of time of sensing for each sensor.

The movement information 136 is information that indicates the state of the person 80 sensed by an indoor sensor 112, Specifically, the movement information 136 indicates whether the state of the person 80 is a moving state or a resting state.

Specific examples of the positional information 134 and the movement information 136 will be described later together with specific operations.

Figures 3, 4:
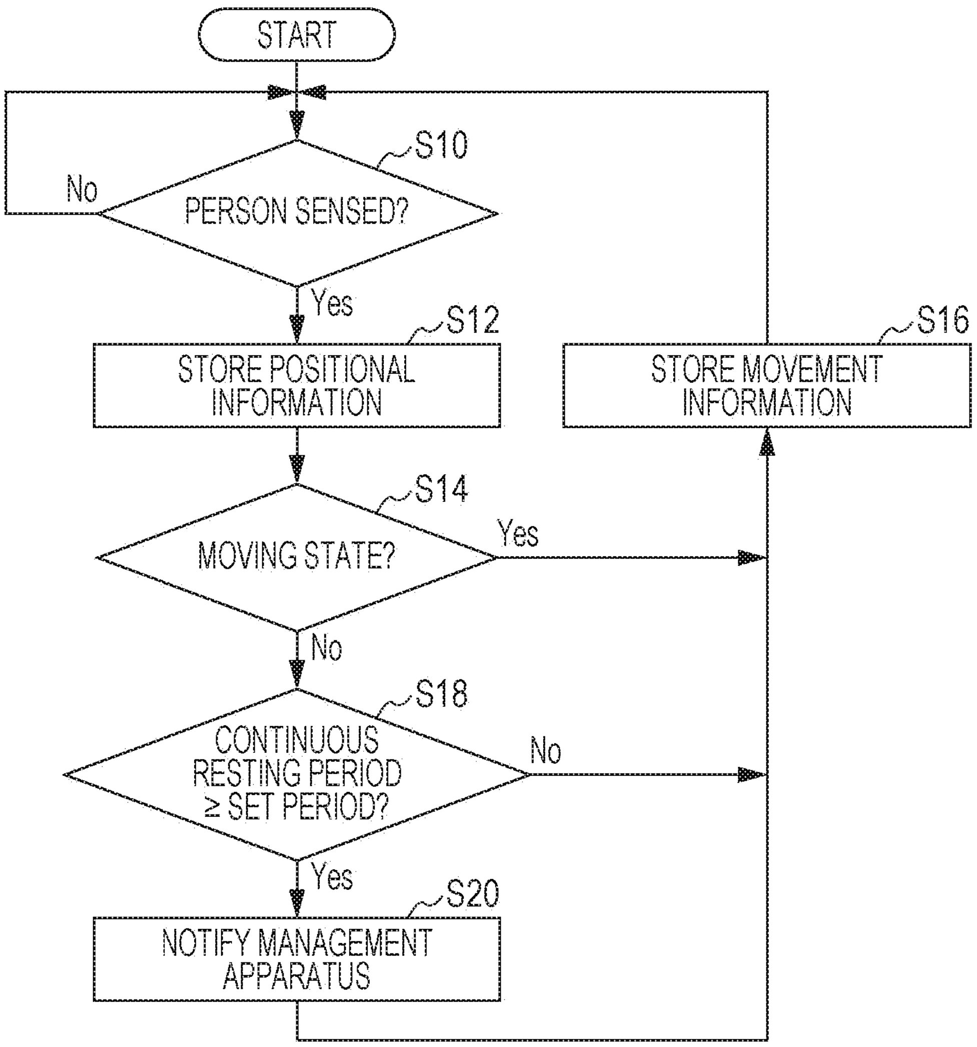
FIG. 3 is a diagram showing an example of walking information stored in a storage of a purifying apparatus according to Embodiment 1.
FIG. 4 is a flow chart showing an operation that the purifying apparatus according to Embodiment 1 performs in a case where no purification command has been acquired.

As shown in FIG. 3, the walking information 138 indicates the walking speed of the person 80, who is in the room. It should be noted that FIG. 3 is a diagram showing an example of walking information 138 stored in the storage 130 of the purifying apparatus 102 according to the present embodiment.

The walking speed indicated by the walking information 138 is for example the average of walking speeds by age. For example, in a case where the space 90 is a living room of a nursing home, the person 80 is an elderly person. Therefore, for example, the walking information 138 indicates, as the walking speed of the person 80, the average of walking speeds of elderly persons in their seventies to eighties. Utilizing a representative numerical value such as an average makes it possible to utilize the walking information 138 on an "as is" basis without updating even in a case where another person has replaced the person 80 to utilize the space 90.

The walking information 138 may indicate a walking speed that is unique to the person 80, i.e. the walking speed of an individual. For example, when the person 80 in the space 90 such as a nursing home is always the same person, the person 80 sensed by the indoor sensors 112 is substantially the same person. Therefore, with the walking information 138 indicating the walking speed of an individual, a judgment can be made with a high degree of accuracy as to whether the person 80 enters the path of travel of the agent.

The purifier 140 is an example of an ejector that ejects ejected matter. For example, the purifier 140 is locally ejects the agent toward an intended position. Specifically, the purifier 140 ejects the agent in a case where a purification command has been acquired by the controller 120. In the present embodiment, the purifier 140 ejects, toward the intended position, a vortex ring 148 formed by a gas containing the agent.

As shown in FIG. 1, the purifier 140 includes a reservoir 142, a hollow 144, and the ejection port 146. The reservoir 142 is a container in which the agent is stored. The hollow 144 is a space in which a gas for forming the vortex rings 148 is stored. The ejection port 146 is an opening that connects the hollow 144 to the outside and through which the vortex rings 148 are ejected.

The hollow 144 is provided, for example, with a structure (not illustrated) that instantaneously changes the content in order to push out the gas from inside. For example, the hollow 144 has provided therein a membrane member having elasticity and a hitting device that deforms the membrane member by hitting it. Instantaneous deformation of the membrane member by the hitting device causes the gas to be pushed out through the ejection port 146. When the gas pushed out from the hollow 144 passes through the ejection port 146, vortex rings 148 are formed and ejected in a predetermined direction.

The ejection port 146 can turn around and face, for example, upward, downward, rightward, or leftward. This allows the purifier 140 to eject vortex rings 148 toward a plurality of intended positions.

The communicator 150 performs communication with an external apparatus. Specifically, the communicator 150 performs communication with the management apparatus 152 by cable or by radio. For example, the communicator 150 performs wireless communication conforming to a wireless communication standard such as Wi-Fi (registered trademark), Bluetooth (registered trademark), or ZigBee (registered trademark). The communicator 110 and the communicator 150 may be implemented as an identical communication interface.

The management apparatus 152 is an example of an external apparatus connected via the communicator 150. For example, the management apparatus 152 is disposed in an administration office in which a care worker who takes care of a resident of a nursing home stays, a so-called nurse center of a hospital, or the like.

Upon receiving a predetermined signal from the purifying apparatus 102 via the communicator 150, the management apparatus 152 performs a notification process for making notification of a possibility that an abnormality might have occurred in the space 90. For example, the management apparatus 152 is connected to a display device or a speaker (not illustrated) and, by causing the display device or the speaker to output an image or a sound, notifies the administrator or the like of a possibility that an abnormality might have occurred.

The inputter 160 accepts an operation input from an outside source to the purifying apparatus 102. The inputter 160 is implemented, for example, as a touch panel display, a physical button switch, or the like. Alternatively, the inputter 160 may be implemented as a receiver that accepts an operation input from a remote control terminal (remote controller) of the purifying apparatus 102. For example, the purifying apparatus 102 may have its outer-shell housing provided with a button switch serving as the inputter 160 for the execution of purification. In a case where the button switch has been depressed, the command generator 124 may generate a purification command.

Further, the inputter 160 may accept the inputting of conditions such as the concentration of the agent, the number of times a vortex ring 148 is ejected, the air volume of a vortex ring 148, and the like. The inputter 160 may accept the inputting of schedule information.

Operation

Next, operations that the purifying apparatus 102 according to the present embodiment performs are described. First, an operation that the purifying apparatus 102 performs in a case where no purification command has been acquired is described with reference to FIGS. 4 and 5.

FIG. 4 is a flow chart showing an operation that the purifying apparatus 102 according to the present embodiment performs in a case where no purification command has been received. The operation shown in FIG. 4 is executed mainly by the sensor controller 122.

The sensor controller 122 waits until the person 80 is sensed (No in S10). Specifically, the sensor controller 122 waits until it receives a sensing signal from at least one of the plurality of indoor sensors 112 via the communicator 110.

Upon sensing of the person 80 (Yes in S10), i.e. upon receiving a sensing signal via the communicator 110, the sensor controller 122 generates positional information 134 on the person 80 on the basis of the sensing signal thus received and stores the positional information 134 in the storage 130 (S12).

Next, the sensor controller 122 judges, on the basis of the positional information 134, the state of the person 80 thus sensed (S14). Specifically, the sensor controller 122 judges whether the state of the person 80 thus sensed is a moving state or a resting state. In a case where the state of the person 80 is a moving state (Yes in S14), the sensor controller 122 stores, in the storage 130, movement information 136 indicating the moving state (S16).

In a case where the state of the person 80 is a resting state (No in S14), the sensor controller 122 judges whether a continuous resting period is not shorter than a set period (S18), The continuous resting period is a period of time during which after the state of the person 80 has been judged to be a resting period, the state of the person 80 is continuously the resting state without being judged as a moving state. The set period is for example a predetermined period of time such as 1 hour.

In a case where the continuous resting period is not shorter than the set period (Yes in S18), the sensor controller 122 outputs a predetermined signal to the management apparatus 152 via the communicator 150 (S20). After having outputted the signal and in a case where the continuous resting period is shorter than the set period (No in S18), the sensor controller 122 stores, in the storage 130, movement information 136 indicating that the state of the person 80 is a resting state (S16).

Since the indoor sensors 112 are always performing sensing of objects, a sensing signal is repeatedly outputted every several seconds or every 1 second or shorter as long as the person 80 is present in any of their sensing regions. For this reason, the sensor controller 122 repeatedly executes the process shown in FIG. 4.

The process for judgment of a moving state and a resting state (S14) is described here in detail with reference to a specific example shown in FIG. 5.

FIG. 5 is a diagram showing an example of positional information 134 and movement information 136 stored in the storage 130 of the purifying apparatus 120 according to the present embodiment. FIG. 5 shows an association between sensing results yielded by two sensors A and B and points of time of sensing. The sensors A and B correspond, for example, to the indoor sensors 112*a* and 112*b*, respectively. Further, the states A and B represent the state of an object first sensed by the sensor A and the state of an object first sensed by the sensor B, respectively.

In the example shown in FIG. 5, the positional information 134 indicates that in the sensing region of the sensor A, an object has been sensed in a position at a distance a at the point of time T1. Furthermore, the positional information 134 indicates that in the sensing region of the sensor A, an object has been sensed in a position at the distance a at the point of time T2. That is, the position of the object sensed at the point of time T1 by the sensor A is the same as the position of the object sensed at the point of time T2 by the sensor A. Therefore, the sensor controller 122 judges that the state of the object is a resting state. The sensor controller 122 generates movement information 136 indicating the resting state at the point of time T2 and stores the movement information 136 in the storage 130.

Similarly, at the point of time T3, objects are sensed by both the sensor A and the sensor B. Specifically, objects are sensed in two places, i.e. a position at a distance b within the sensing region of the sensor A and a position at a distance c within the sensing region of the sensor B, respectively. For example, such a situation as that which takes place at the point of time T3 can take place in a case where two persons are present in the space 90.

Since the point of time T2 and the point of time T3 are different in distance of sensing by the sensor A from each other, the sensor controller 122 judges that the state of the object is a moving state. A possible example of a situation from the point of time T2 to the point of time T3 is a first situation where a person who was in the position at the distance a within the sensing region of the sensor A at the point of time T2 has moved to the position at the distance b and another person has newly appeared in the position at the distance c within the sensing region of the sensor B. Another possible example is a second situation where a person who was in the position at the distance a within the sensing region of the sensor A at the point of time T2 has moved to the position at the distance c within the sensing region of the sensor B and another person has newly appeared in the position at the distance b within the sensing region of the sensor A. Which of the situations has occurred can be estimated, for example, on the basis of a walking speed indicated by the walking information 138. However, since, in either situation, a person is in a sensing region after all and a person who was at the distance a of the sensing region of the sensor A at the point of time T2 has moved after all, it is not necessary to identify which of the situations has occurred.

At the point of time T4, the sensors A and B are different in distance within their sensing regions from each other. Therefore, the sensor controller 122 judges that the states of two objects sensed by the sensors A and B, respectively, are both moving states.

At the point of time T5, no object is sensed by the sensor A, but two objects are sensed by the sensor B. For example, a case where a person who was at a distance d within the sensing region of the sensor A has moved to a position at a distance f within the sensing region of the sensor B can be assumed. In this case, the object sensed at a distance e within the sensing region of the sensor B at the point of time T4 stays at the distance e. Therefore, the sensor controller 122 judges that the state of the object sensed by the sensor A is a moving state and the state of the object sensed by the sensor B is a resting state.

In this way, the sensor controller 122 can determine the state of an object on the basis of sensing results yielded by the indoor sensors 112. Further, the sensor controller 122 can determine an approximate moving direction of an object from positions at multiple points of time.

Next, an operation that the purifying apparatus 102 performs in a case where a purification command has been acquired is described with reference to FIG. 6.

Figure 6:
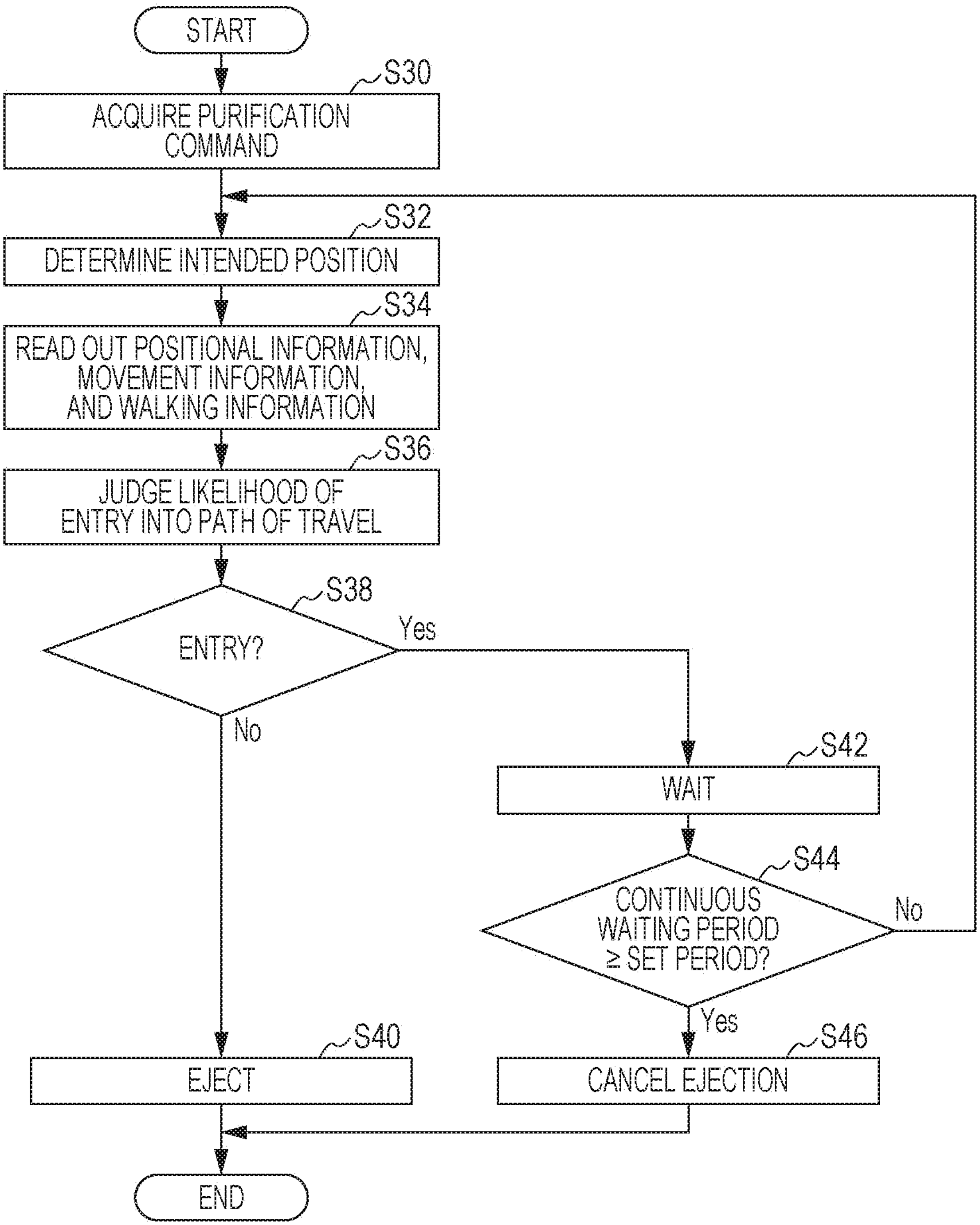
FIG. 6 is a flow chart showing an operation that the purifying apparatus according to Embodiment 1 performs in a case where a purification command has been acquired.

FIG. 6 is a flow chart showing an operation that the purifying apparatus 102 according to the present embodiment performs in a case where a purification command has been acquired. The operation shown in FIG. 6 is executed mainly by the purification controller 126.

First, the purification controller 126 acquires a purification command (S30), The purification command is generated by the command generator 124 at a timing based on the schedule information or a timing at which an external input was received.

Next, the purification controller 126 determines an intended position that the ejected matter is made to reach (S32). Specifically, the purification controller 126 determines a predetermined position as the intended position. For example, the storage 130 may have stored therein intended position information indicating predetermined positions such as the handle 93 and the door knob 94. The purification controller 126 determines a predetermined position as the intended position by reading out the intended position information from the storage 130. In a case where there are a plurality of predetermined positions, the purification controller 126 selects one position from among the plurality of positions and determines, as the intended position, the positions thus selected. Alternatively, the purification controller 126 may determine, as the intended position, a position accepted via the inputter 160. Further, the purification command may contain information indicating the intended position. The purification controller 126 may determine the intended position on the basis of the purification command.

It should be noted that the determination of the intended position (S32) may precede the acquisition of the purification command (S30). Alternatively, the determination of the intended position (S32) may be preceded by the readout of positional information 134 (S34).

Next, the purification controller 126 reads out positional information 134, movement information 136, and walking information 138 from the storage 130 (S34). For example, the purification controller 126 reads out positional information 134 and movement information 136 associated with multiple points of time nearest to the point of time at which the purification command was acquired.

Next, the purification controller 126 judges the likelihood of entry of the person 80 into the path of travel of the agent (S36). Specifically, the purification controller 126 determines a path of flight of vortex rings 148 as the path of travel of the agent on the basis of a positional relationship between the intended position designated by the purification command and the ejection port 146. Furthermore, the purification controller 126 determines the position of the person 80 at the point in time at which the purification command was acquired and the moving direction of the person 80 from the positional information 134 and the movement information 136. On the basis of the position and moving direction thus determined and the walking speed indicated by the walking information 138, the purification controller 126 judges whether the person 80 thus sensed enters the path of travel within a required period of time required for the agent to reach the intended position.

In a case where the purification controller 126 has judged that the person 80 does not enter the path of travel (No in S38), the purification controller 126 ejects the agent toward the intended position by causing the purifier 140 to eject vortex rings 148 (S40).

In a case where the purification controller 126 has judged that the person 80 enters the path of travel (Yes in S38), the purification controller 126 waits ejection for a predetermined period of time such as several seconds (S42). In a case where a continuous waiting period is shorter than a set period (No in S44), the purification controller 126 returns to step S32 to determine an intended position, read out information from the storage 130, and judge the likelihood of entry. The continuous waiting period is a period of time during which a waiting state has continued without ejection of a vortex ring 148 since an ejection command was acquired. The set period here is a predetermined period of time such as not shorter than several tens of seconds and not longer than several minutes such as 30 seconds.

Normally, during several seconds or several minutes of waiting, the person 80 moves and no longer enters the path of travel. Therefore, repeating a judgment of the likelihood of entry more than once allows the purifying apparatus 102 to eject the agent at a timing at which the ejection of the agent has become possible.

In a case where the continuous waiting period is not shorter than the set period (Yes in S44), the purification controller 126 cancels the ejection of the agent (S46). For example, in a case where the person 80 is working on the path of travel, the person 80 may not move right away. In a case where the ejection of the agent has been canceled, the operation shown in FIG. 6 is executed upon acquisition of a next purification command, so that the intended position is purified.

As noted above, the purifying system 100 and the purifying apparatus 102 according to the present embodiment restrict the ejection of the agent in a case where the likelihood of entry of an object into the path of travel of the agent is high. This makes it possible to prevent the agent from being no longer conveyed to an intended position. Since a portion of the agent that is not conveyed to the intended position can be reduced, the agent can be efficiently used. Further, since the agent can be ejected at such a timing that an object does not interfere with the path of travel, a sufficient amount of the agent can be conveyed to the intended position, so that the intended position can be efficiently purified.

Embodiment 2

Next, Embodiment 2 is described.

Embodiment 1 has illustrated a case where the person 80, who is an example of an object that interferes with the path of travel of the agent, is present in the same space 90 as the purifying apparatus 102 and an intended position. On the other hand, Embodiment 2 illustrates a case where an object that interferes with the path of travel of the agent is present outside the space 90. It should be noted that the following gives a description with a focus on differences from Embodiment 1 and omits or simplifies a description of common features.

Figure 7:
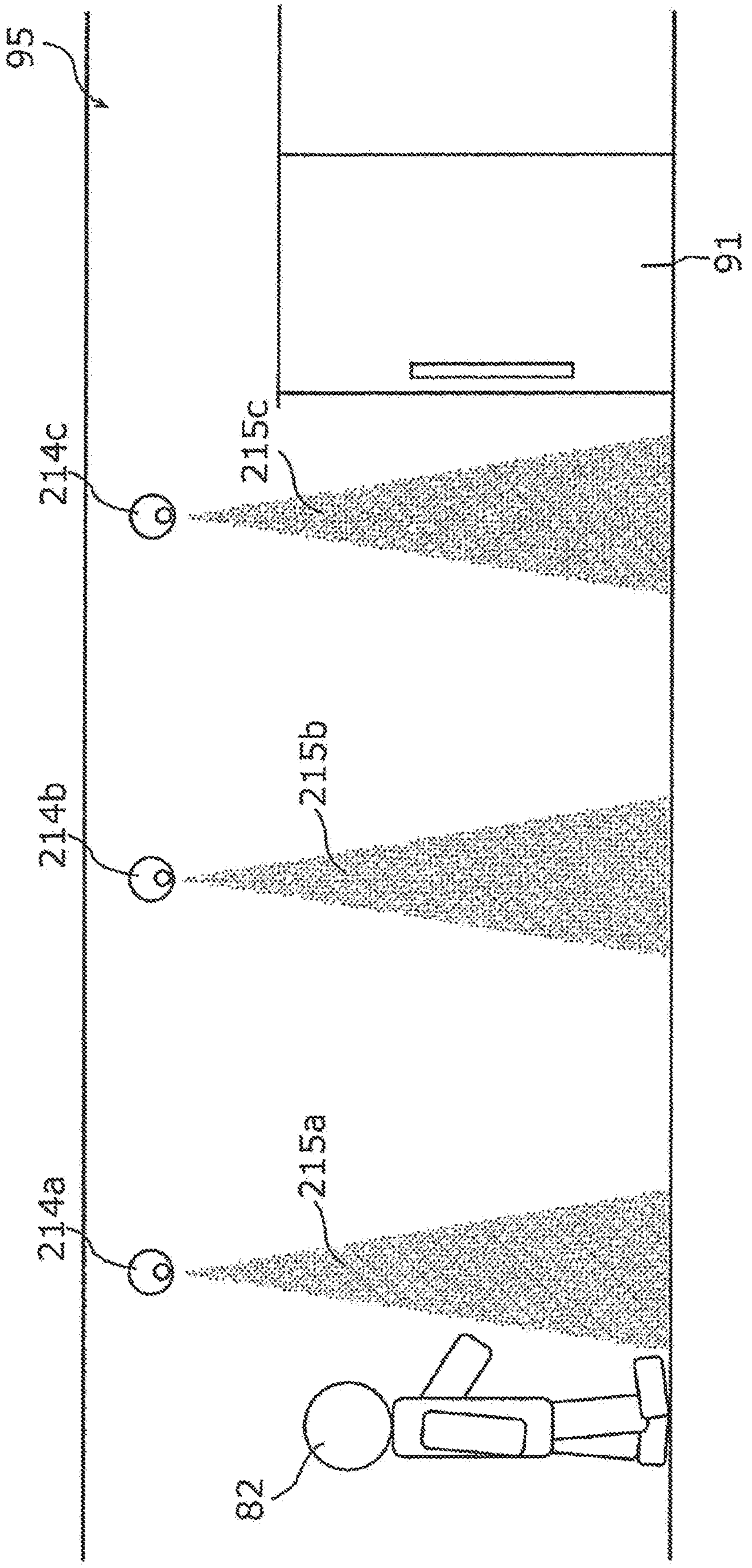
FIG. 7 is a diagram showing the outside of a space to which a purifying system according to Embodiment 2 is applied.

FIG. 7 is a diagram showing the outside of a space 90 to which a purifying system 200 (see FIG. 8) according to the present embodiment is applied. For example, FIG. 7 shows an outer space 95 out of the door 91 of the space 90 shown in FIG. 1.

Specifically, the space 95 is a space separated by the door 91 from the space 90 in which a purifying apparatus 202 (see FIG. 8) is disposed. The space 90 is an example of a first space in which the purifying apparatus 202 is disposed. The space 95 is an example of a second space separated by the door 91 from the space 90. Specifically, while the space 90 is an indoor space, the space 95 is an outdoor space. The space 95 is for example a corridor that leads to the space 90, but may be a living room that is different from the space 90. Further, although an area outside the door 91 is shown here, the same applies to the door 92 shown in FIG. 1.

FIG. 7 shows a person 82 walking toward the door 91. In a case where the handle 93 of the door 91 is an intended position to be purified, the intended position is moved by the person 82 opening and closing the door 91. This poses a risk that a portion of the agent that has been ejected may not be conveyed to the intended position. Thus, an object that interferes with the path of travel of the agent is not always present in the same space as an intended position and the purifying apparatus 202 (see FIG. 8).

To address this problem, the purifying system 200 according to the present embodiment conveys the agent to an intended position and purifies the intended position with the agent thus conveyed even in a case where the person 82 is present in the space 95 outside the space 90 in which the purifying apparatus 202 (see FIG. 8) is disposed.

Configuration

Next, a configuration of the purifying system 200 according to the present embodiment is described with reference to FIG. 8.

Figure 8:
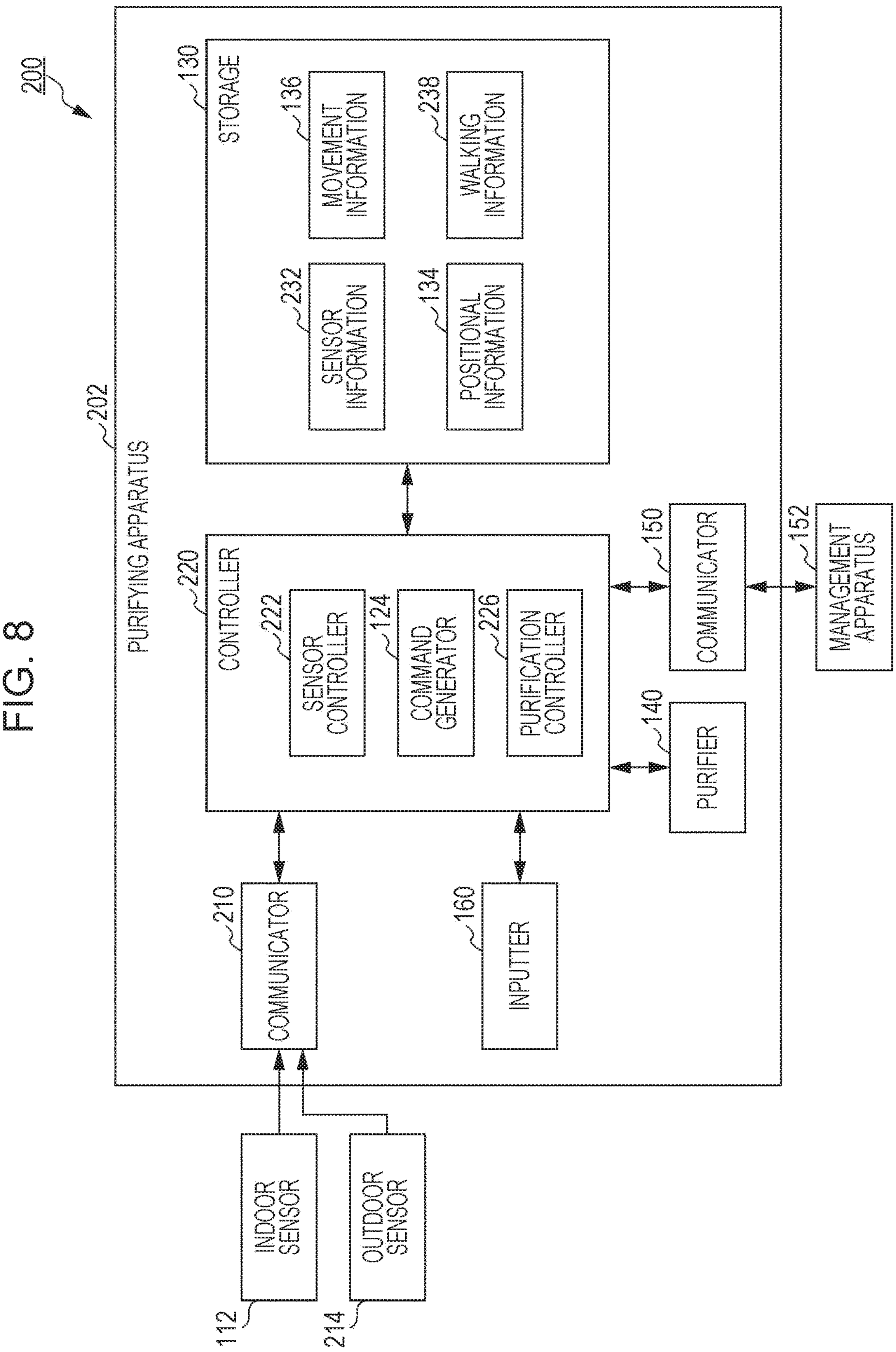
FIG. 8 is a block diagram showing a configuration of the purifying system according to Embodiment 2.

FIG. 8 is a block diagram showing a configuration of the purifying system 200 according to the present embodiment. As shown in FIG. 8, the purifying system 200 includes the purifying apparatus 202, one or more indoor sensors 112, one or more outdoor sensors 214, and a management apparatus 152.

The one or more outdoor sensors 214 are each an example of a first sensor and are disposed in the space 95. The one or more outdoor sensors 214 are human sensors that detect the position of the person 82.

FIG. 7 illustrates three outdoor sensors 214*a*, 214*b*, and 214*c* as the one or more outdoor sensors 214. The three outdoor sensors 214*a*, 214*b*, and 214*c* each have the same configuration. In the following description, the three outdoor sensors 214*a*, 214*b*, and 214*c* are collectively referred to as "outdoor sensors 214" in a case where no particular distinction is made among the three outdoor sensors 214*a*, 214*b*, and 214*c*. The number of outdoor sensors 214 that the purifying system 200 includes may be 1 or 2 or not smaller than 4.

Each of the outdoor sensors 214 is for example an infrared sensor having a predetermined sensing region. The outdoor sensor 214 outputs a sensing signal upon entry of the person 82 into the sensing region. The sensing signal is acquired by a controller 220 of the purifying apparatus 202 via a communicator 210 of the purifying apparatus 202.

In FIG. 7, the three outdoor sensors 214*a*, 214*b*, and 214*c* have their respective sensing regions 215*a*, 215*b*, and 215*c* indicated by half-tone dot meshing. The sensing regions 215*a*, 215*b*, and 215*c* are different from one another. The sensing regions 215*a*, 215*b*, and 215*c* may partly overlap.

The sensing region 215*a* is formed in a position most distant of the plurality of sensing regions from the door 91. The sensing region 215*c* is formed in a position nearest of the plurality of sensing regions to the door 91. The sensing region 215*b* is formed between the sensing region 215*a* and the sensing region 215*c*.

In the present embodiment, each outdoor sensor 214 is assigned a unique identifier for identification of the plurality of outdoor sensors 214. A sensing signal contains an identifier that is unique to an outdoor sensor that outputs the sensing signal. The identifiers of the outdoor sensors 214 are assigned in such a manner as not to coincide with the identifiers of the indoor sensors 112. This allows the purifying apparatus 202 to identify, on the basis of an identifier contained in a sensing signal, an indoor sensor 112 and an outdoor sensor 214 from which the sensing signal was transmitted.

For example, assume a case where the person 82 walks toward the door 91 as shown in FIG. 7. At this point in time, a sensing signal is outputted from the outdoor sensor 214*a*, as the person 82 enters the sensing region 215*a* first. Next, a sensing signal is outputted from the outdoor sensor 214*b*, as the person 82 enters the sensing region 215*b*. Finally, a sensing signal is outputted from the outdoor sensor 214*c*, as the person 82 enters the sensing region 215*c*.

At this point in time, the purifying apparatus 202, which has received the sensing signals in sequence, finds that the order of the sensing signals thus received is the order of the outdoor sensor 214*a*, the outdoor sensor 214*b*, and the outdoor sensor 214*c*. This allows the purifying apparatus 202 to find that the person 82 is approaching the door 91, Further, the moving speed of the person 82 can be calculated on the basis of the points of time at which the sensing signals were received.

The outdoor sensors 214 do not need to be infrared sensors but may be image sensors or ranging sensors.

As shown in FIG. 8, the purifying apparatus 202 differs from the purifying apparatus 102 according to Embodiment 1 in that the purifying apparatus 202 includes the communicator 210 and the controller 220 instead of the communicator 110 and the controller 120. Further, the storage 130 has stored therein sensor information 232 and walking information 238 instead of the sensor information 132 and the walking information 138.

The communicator 210 performs communication with each of the plurality of indoor sensors 112 and the plurality of outdoor sensors 214 by cable or by radio. For example, the communicator 210 performs wireless communication conforming to a wireless communication standard such as Wi-Fi (registered trademark), Bluetooth (registered trademark), or ZigBee (registered trademark). The communicator 210 acquires sensing signals from each of the plurality of indoor sensors 112 and each of the plurality of outdoor sensors 214. The sensing signals thus acquired are outputted to a sensor controller 222 of the controller 220.

As shown in FIG. 8, the controller 220 includes the sensor controller 222, a command generator 124, and a purification controller 226. The controller 220 is achieved, for example, by a nonvolatile memory in which a program is stored, a volatile memory serving as a transitory recording region in which to execute the program, an I/O port, a processor that executes the program, or other components. The sensor controller 222, command generators 124, and purification controller 226 of the controller 220 may each be implemented as software that is executed by the processor or may each be implemented as hardware such as an electronic circuit including a plurality of circuit elements.

The sensor controller 222 controls operations involving the indoor sensors 112 and the outdoor sensors 214. Specifically, the sensor controller 222 generates positional information 134 on the person 80 or the person 82 on the basis of a sensing signal outputted from each of the indoor sensors 112 or the outdoor sensors 214 and stores the positional information 134 in the storage 130. A specific operation of the sensor controller 222 is the same as that of Embodiment 1.

The purification controller 226 controls the purifier 140. As in the case of Embodiment 1, the purification controller 226 judges the likelihood of interference by judging the likelihood of entry of the person 80 into the space 90. Furthermore, the purification controller 226 judges the likelihood of interference by judging whether the person 82 outside the space 90 approaches the door 91 within the required period of time, i.e. by judging the likelihood of approach. That is, in the present embodiment, the term "interference" encompasses the approach of the person 82 to the door 91.

For example, upon reading out positional information 134 from the storage 130, the purification controller 226 judges the likelihood of entry if the position of a person indicated by the positional information 134 thus read out is the space 90. The purification controller 226 judges the likelihood of approach if the position of a person indicated by the positional information 134 thus read out is the space 95. If, for example in a case where a plurality of persons are present, the positional information 134 thus read out indicates both the spaces 90 and 95 as the positions of the persons, the purification controller 226 judges both the likelihood of entry and the likelihood of approach.

In a case where the purification controller 226 has judged that the person 82 approaches the door 91, the purification controller 226 restricts the ejection of the ejected matter by the purifier 140. Specifically, in a case where the purification controller 226 has judged that the person 82 approaches the door 91, the purification controller 226 restricts the ejection of the agent by the purifier 140.

In a case where the purification controller 226 has judged that the person 82 does not approach the door 91, the purification controller 226 causes the purifier 140 to eject the ejected matter. Specifically, in a case where the purification controller 226 has judged that the person 82 does not approach the door 91, the purification controller 226 causes the purifier 140 to eject the agent by ejecting a vortex ring 148. Specific operations for restricting the ejection and ejecting the agent are the same as those of Embodiment 1.

The sensor information 232 indicates an association between the respective identifiers of the plurality of indoor sensors 112 and the plurality of outdoor sensors 214 connected to the purifying apparats 202 by cable or by radio and the positions of the sensing regions. The sensor information 232 is updated in a case where an indoor sensor 112 or an outdoor sensor 214 has been newly added and a case where the sensing region of an existing indoor sensor 112 or outdoor sensor 214 has been changed.

As shown in FIG. 9, the walking information 238 indicates the walking speeds of the person 80, who is in the room, and the person 82, who is outside the room. It should be noted that FIG. 9 is a diagram showing an example of walking information 238 stored in the storage 130 of the purifying apparatus 202 according to the present embodiment.

The walking speeds indicated by the walking information 238 are for example the averages of walking speeds by age. For example, in a case where the space 90 is a living room of a nursing home, the person 82 is a young care worker. Therefore, for example, the walking information 238 indicates, as the walking speed of the person 82, the average of walking speeds of persons in their twenties to forties. The outdoor speed B is higher than the indoor speed A. Utilizing a representative numerical value such as an average makes it possible to utilize the walking information 238 on an "as is" basis without updating even in a case where another person has replaced the person 82 to move in the space 95.

Operation

Next, operations that the purifying apparatus 202 according to the present embodiment performs are described. An operation that is performed in a case where no purification command has been acquired is the same as that which is performed in the case of Embodiment 1, and is executed by the sensor controller 222 along with the operation shown in FIG. 4.

Figure 10:
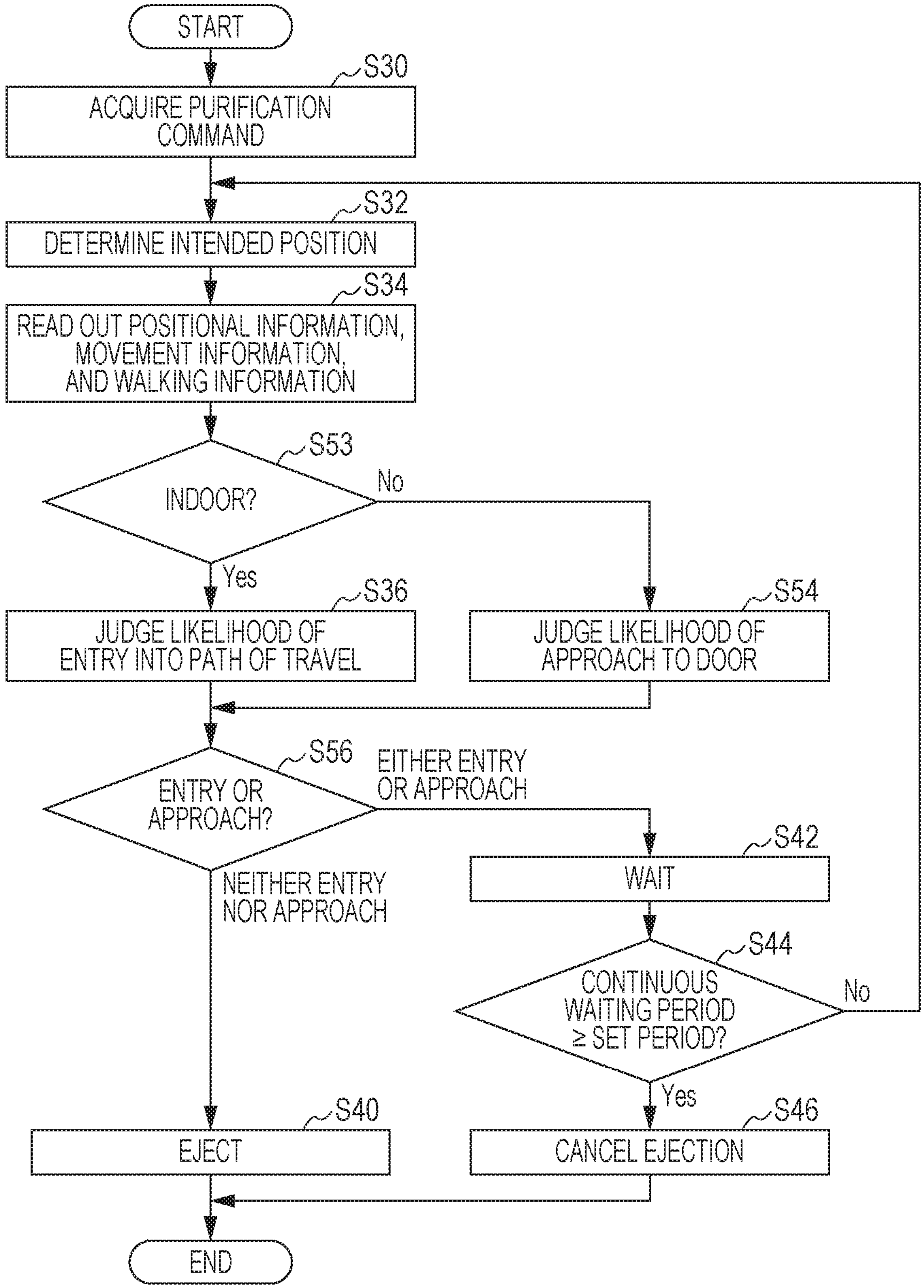
FIG. 10 is a flow chart showing an operation that the purifying apparatus according to Embodiment 2 performs in a case where a purification command has been acquired.

FIG. 10 is a flow chart showing an operation that the purifying apparatus 202 according to the present embodiment performs in a case where a purification command has been acquired. The operation shown in FIG. 10 is executed mainly by the purification controller 226.

As shown in FIG. 10, the process from the acquisition of a purification command (S30) to the readout of information from the storage 130 (S34) is the same as that of Embodiment 1.

The purification controller 226 judges, on the basis of the positional information 134 thus read out, whether the position of the object thus sensed is the indoor space 90 or the outdoor space 95 (S53). Specifically, the purification controller 226 judges whether the positional information 134 thus read out is information based on an indoor sensor 112 or an outdoor sensor 214.

In a case where the position of the object thus sensed is the indoor space 90 (Yes in S53), the purification controller 226 judges the likelihood of entry of the object into the path of travel of the agent (S36). A specific process for judging the likelihood of entry is the same as that of Embodiment 1.

In a case where the position of the object thus sensed is the outdoor space 95 (No in S53), the purification controller 226 judges the likelihood of approach to the door 91 (S54). Specifically, as in the case of a judgment of the likelihood of entry, the purification controller 226 determines, from the positional information 134 and the movement information 136, the position of the person 82 at the point of time at which the purification command was received and the moving direction of the person 82. On the basis of the position and moving direction thus determined and the walking speed indicated by the walking information 238, the purification controller 226 judges whether the person 82 thus sensed reaches the door 91 within a required period of time required for the agent to reach the intended position.

In a case were objects have been sensed in both the space 90 and the space 95, both steps S36 and S54 are executed. That is, in a case where both the person 80 and the person 82 have been sensed, the purification controller 226 judges both the likelihood of entry and the likelihood of approach.

In a case where the purification controller 226 has judged that the person 80 does not go onto the path of travel and that the person 82 does not approach the door 91, i.e. that there is no likelihood of entry or approach ("NEITHER ENTRY NOR APPROACH" in S56), the purification controller 226 ejects the agent toward the intended position by causing the purifier 140 to eject vortex rings 148 (S40).

In a case where the purification controller 226 has judged that there is a likelihood of at least either entry or approach ("EITHER ENTRY OR APPROACH" in S56), the purification controller 226 waits the ejection for a predetermined period of time such as several seconds (S42). The subsequent process is the same as that of Embodiment 1.

As noted above, the purifying system 200 and the purifying apparatus 202 according to the present embodiment restrict the ejection of the agent in a case where the likelihood of approach of an object to the door 91 is high. This makes it possible to prevent the agent from being no longer conveyed to an intended position. Since a portion of the agent that is not conveyed to the intended position can be reduced, the agent can be efficiently used. Further, since the agent can be ejected at such a timing that an object does not interfere with the path of travel, a sufficient amount of the agent can be conveyed to the intended position, so that the intended position can be efficiently purified.

In the present embodiment, the handles 93 of the door 91 does not need to be an intended position. For example, the door knob 94 of the door 92 may be an intended position, Even in this case, in a case where the door 91 is opened and closed, a change in airflow due to the opening and closing might bend the path of travel of a vortex ring 148. This problem can be addressed by judging the likelihood of approach to the door 91 and thereby ejecting the agent at such a timing that the door 91 is not opened or closed.

Embodiment 3

Next, Embodiment 3 is described.

Embodiments 1 and 2 have illustrated an example in which an intended position to be purified is a predetermined position. On the other hand, Embodiment 3 illustrates a case where an intended position is determined on the basis of a result of sensing involving the use of a sensor. It should be noted that the following gives a description with a focus on differences from Embodiment 1 or 2 and omits or simplifies a description of common features.

Figure 11:
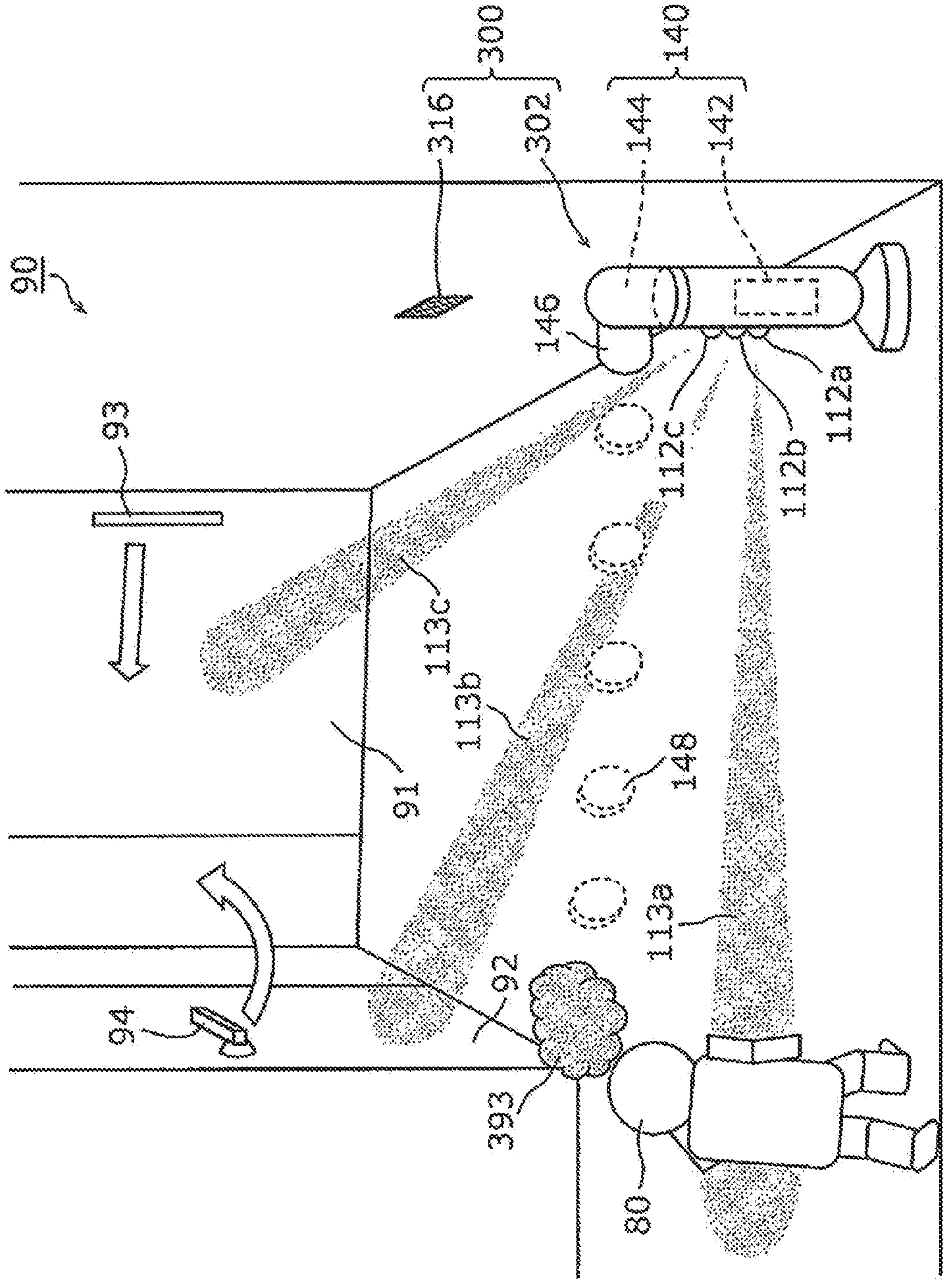
FIG. 11 is a diagram presenting an overview of a purifying system according to Embodiment 3.

FIG. 11 is a diagram presenting an overview of a purifying system 300 according to the present embodiment. FIG. 11 schematically shows an aerosol 393 floating in the space 90.

The aerosol 393 contains droplets scattered out of the mouth of the person 80, for example, by the person 80 coughing or sneezing. In a case where the person 80 is suffering from a disease, the droplets are highly likely to contain viruses or bacteria. That is, the aerosol 393 is highly likely to contain viruses or bacteria floating in the space 90.

An intended position to be purified by the purifying system 300 according to the present embodiment is a position in which the aerosol 393 is contained. Since the aerosol 393 is floating in the space 90, the position of the aerosol 393 is not fixed but changeable. To address this problem, the purifying system 300 includes a second sensor for detecting the position of the aerosol 393. Alternatively, the aerosol 393 may be pollen, PM 2.5, or the like.

Configuration

Figure 12:
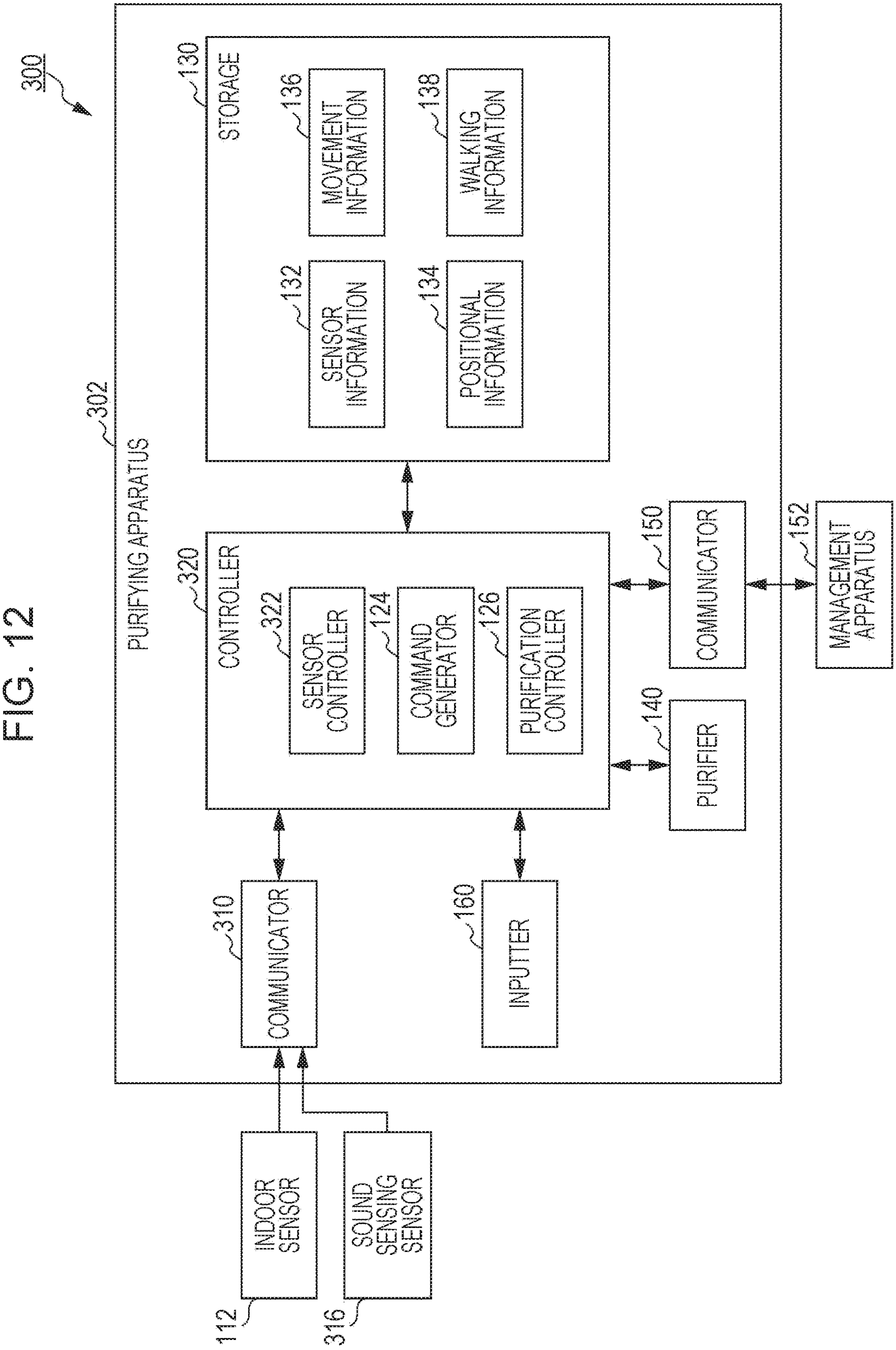
FIG. 12 is a block diagram showing a configuration of the purifying system according to Embodiment 3.

The following describes a configuration of the purifying system 300 according to the present embodiment with reference to FIG. 12.

FIG. 12 is a block diagram showing a configuration of the purifying system 300 according to the present embodiment. As shown in FIG. 12, the purifying system 300 differs from the purifying system 100 according to Embodiment 1 in that the purifying system 300 includes a purifying apparatus 302 instead of the purifying apparatus 102 and further includes a sound sensing sensor 316.

The sound sensing sensor 316 is an example of a second sensor for detecting a position in which the aerosol 393 is present. The sound sensing sensor 316 is for example a microphone that senses a sound produced by the person 80. Specifically, the sound sensing sensor 316 is a microphone that has directivity in a plurality of directions, and detects the position of the source of generation of a sound. For example, the sound sensing sensor 316 senses a sound that is generated when the person 80 coughs or sneezes, and detects the position of the source of generation of the sound. The sound sensing sensor 316 outputs a sensing signal containing positional information indicating the position of the source of generation of the sound.

As shown in FIG. 11, the sound sensing sensor 316 is provided on a wall, a ceiling, or the like that constitutes the space 90. As is the case with the indoor sensors 112, the sound sensing sensor 316 may be integrated with the purifying apparatus 302.

As shown in FIG. 12, the purifying apparatus 302 differs from the purifying apparatus 102 according to Embodiment 1 in that the purifying apparatus 302 includes a communicator 310 and a controller 320 instead of the communicator 110 and the controller 120.

The communicator 310 performs communication with each of the plurality of indoor sensors 112 and the sound sensing sensor 316 by cable or by radio. For example, the communicator 310 performs wireless communication conforming to a wireless communication standard such as Wi-Fi (registered trademark), Bluetooth (registered trademark), or ZigBee (registered trademark). The communicator 310 acquires sensing signals from each of the plurality of indoor sensors 112 and the sound sensing sensor 316. The sensing signals thus acquired are outputted to a sensor controller 322 of the controller 320.

As shown in FIG. 12, the controller 320 includes the sensor controller 322, a command generator 124, and a purification controller 126. The controller 320 is achieved, for example, by a nonvolatile memory in which a program is stored, a volatile memory serving as a transitory recording region in which to execute the program, an I/O port, a processor that executes the program, or other components. The sensor controller 322, command generators 124, and purification controller 126 of the controller 320 may each be implemented as software that is executed by the processor or may each be implemented as hardware such as an electronic circuit including a plurality of circuit elements.

The sensor controller 322 controls operations involving the indoor sensors 112 and the sound sensing sensor 316. The operation involving the indoor sensors 112 is the same as that of Embodiment 1. In the present embodiment, the sensor controller 322 further determines an intended position on the basis of a sensing signal outputted from the sound sensing sensor 316. Specifically, the sensor controller 322 acquires, from a sensing signal outputted from the sound sensing sensor 316, positional information indicating the position of the source of generation of a sound produced by a cough or sneeze of the person 80 and, on the basis of the positional information thus acquired, determines, as the intended position, the position of the aerosol 393 containing droplets scattered by coughing or sneezing.

For example, the sensor controller 322 determines, as the intended position, a position included in a predetermined range centered at the position indicated by the positional information. The predetermined range is a range that is defined by the scattering distance of droplets. Since droplets scattered by sneezing scatter farther than droplets scattered by coughing, the predetermined range may be larger in the case of sneezing than in the case of coughing. The predetermined range is a range of several tens of centimeters to several meters. The sensor controller 322 may determine, as the intended position, the position indicated by the positional information.

The foregoing configuration allows the purifying system 300 according to the present embodiment to efficiently remove bacteria or viruses coughed or sneezed into the space 90 and floating in the space 90. Since a sound produced by coughing or sneezing can be sensed by the sound sensing sensor 316 no matter where in the space 90 the person 80 is present, bacteria or viruses can be efficiently removed.

The operation of the purifying system 300 according to the present embodiment is the same as the operation of the purifying system 100 according to Embodiment 1. In this case, the operation shown in FIG. 6 may be started upon sensing of a cough or sneeze of the person 80 by the sound sensing sensor 316. For example, the command generator 124 may generate a purification command upon sensing of a cough or sneeze of the person 80 by the sound sensing sensor 316.

Alternatively, as a second sensor for determining an intended position, a type of sensor that is different from the sound sensing sensor 316 can be used in addition to or instead of the sound sensing sensor 316. The following describes modifications of the purifying system 300 according to the present embodiment.

Modification 1

First, Modification 1 of the present embodiment is described with reference to FIG. 13.

Figure 13:
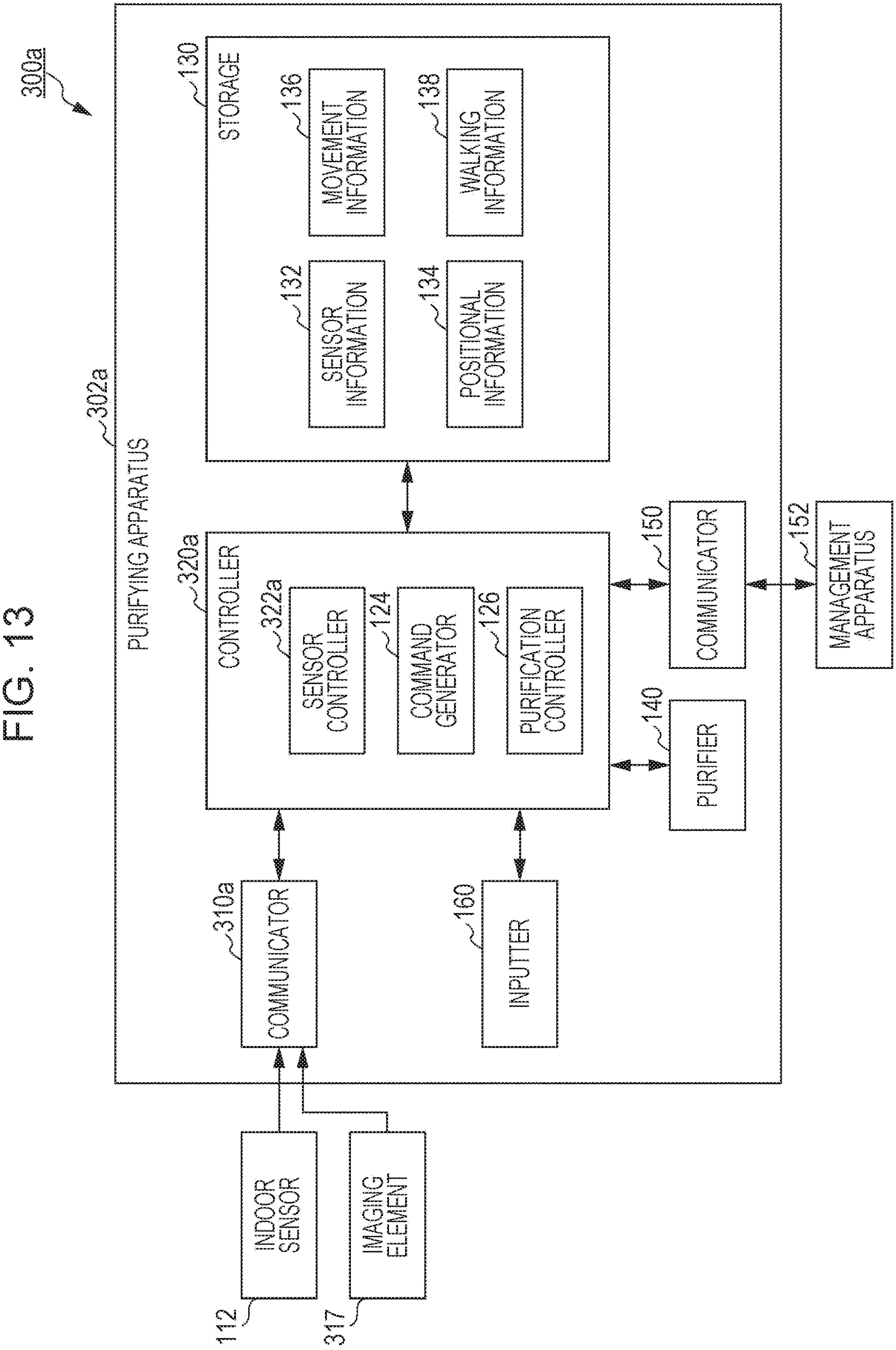
FIG. 13 is a block diagram showing a configuration of a purifying system according to Modification 1 of Embodiment 3.

FIG. 13 is a block diagram showing a configuration of a purifying system 300*a* according to the present modification. As shown in FIG. 13, the purifying system 300*a* differs from the purifying system 300 shown in FIG. 12 in that the purifying system 300*a* includes a purifying apparatus 302*a* and an imaging element 317 instead of the purifying apparatus 302 and the sound sensing sensor 316.

The imaging element 317 is an example of a second sensor for detecting a position in which the aerosol 393 is present. The imaging element 317 is for example an image sensor that generates a moving image by taking images of the person 80. The imaging element 317 outputs a generated moving image to the purifying apparatus 302*a*.

As is the case with the sound sensing sensor 316 shown in FIG. 12, the imaging element 317 is provided on a wall, a ceiling, or the like that constitutes the space 90. As is the case with the indoor sensors 112, the imaging sensor 317 may be integrated with the purifying apparatus 302*a*.

As shown in FIG. 13, the purifying apparatus 302*a* differs from the purifying apparatus 302 shown in FIG. 12 in that the purifying apparatus 302*a* includes a communicator 310*a* and a controller 320*a* instead of the communicator 310 and the controller 320.

The communicator 310*a* performs communication with each of the plurality of indoor sensors 112 and the imaging element 317 by cable or by radio. For example, the communicator 310*a* performs wireless communication conforming to a wireless communication standard such as Wi-Fi (registered trademark), Bluetooth (registered trademark), or ZigBee (registered trademark). The communicator 310*a* acquires a sensing signal from each of the plurality of indoor sensors 112 and acquires a moving image from the imaging element 317. The sensing signals thus acquired and the moving image thus acquired are outputted to a sensor controller 322*a* of the controller 320*a*.

As shown in FIG. 13, the controller 320*a* includes the sensor controller 322*a*, a command generator 124, and a purification controller 126. The controller 320*a* is achieved, for example, by a nonvolatile memory in which a program is stored, a volatile memory serving as a transitory recording region in which to execute the program, an I/O port, a processor that executes the program, or other components. The sensor controller 322*a*, command generators 124, and purification controller 126 of the controller 320*a* may each be implemented as software that is executed by the processor or may each be implemented as hardware such as an electronic circuit including a plurality of circuit elements.

The sensor controller 322*a* controls operations involving the indoor sensors 112 and the imaging element 317. The operation involving the indoor sensors 112 is the same as that of Embodiment 1. In the present embodiment, the sensor controller 322*a* further determines an intended position on the basis of a moving image outputted from the imaging element 317. Specifically, the sensor controller 322*a* detects an action of the person 80 on the basis of a moving image outputted from the imaging element 317. More specifically, the sensor controller 322*a* detects a sneeze or cough of the person 80. For example, in a case where the person 80 has performed an action of vertically shaking his/her face, the sensor controller 322*a* detects the action as a sneeze of the person 80. Further, for example, in a case where the person 80 has performed an action of covering his/her mouth with his/her hand, the sensor controller 322*a* detects the action as a cough of the person 80, It should be noted that examples of operations for detecting a cough or a sneeze are not limited to these examples.

Further, the purifying system 300*a* may include the sound sensing sensor 316 shown in FIG. 12. A coughing or sneezing action of the person 80 and a position in which the action was performed can be detected with a higher degree of accuracy on the basis of a moving image obtained from the imaging element 317 and a sound obtained from the sound sensing sensor 316. In a case where the position of the person 80 can be detected on the basis of a moving image, the sound sensing sensor 316 may be a non-directional microphone and does not need to be able to detect the position of the source of generation of a sound.

Further, the sensor controller 322*a* determines, as the intended position, the position of the aerosol 393 containing droplets scattering out of the mouth of the person 80 having coughed or sneezed. For example, the sensor controller 322*a* identifies, on the basis of a moving image, the position of the mouth of the person 80 at the time when the person 80 performed an action detected as a cough or a sneeze, and determines, as the intended position, a position included in a predetermined range in front of the position of the mouth. The predetermined range is a range that is defined on the basis of the scattering distance of droplets. The sensor controller 322 may determine the position of the mouth of the person 80 as the intended position.

The foregoing configuration allows the purifying system 300*a* according to the present modification to efficiently remove bacteria or viruses coughed or sneezed into the space 90 and floating in the space 90. Since a position in which the person 80 has coughed or sneezed can be detected by the imaging element 317 no matter where in the space 90 the person 80 is present, bacteria or viruses can be efficiently removed.

The operation of the purifying system 300*a* according to the present modification is the same as the operation of the purifying system 100 according to Embodiment 1. In this case, the operation shown in FIG. 6 may be started upon detection of a cough or sneeze of the person 80 by the imaging element 317, For example, the command generator 124 may generate a purification command upon sensing of a cough or sneeze of the person 80 by the imaging element 317.

Modification 2

Next, Modification 2 of the present embodiment is described with reference to FIGS. 14 and 15.

Figure 14:
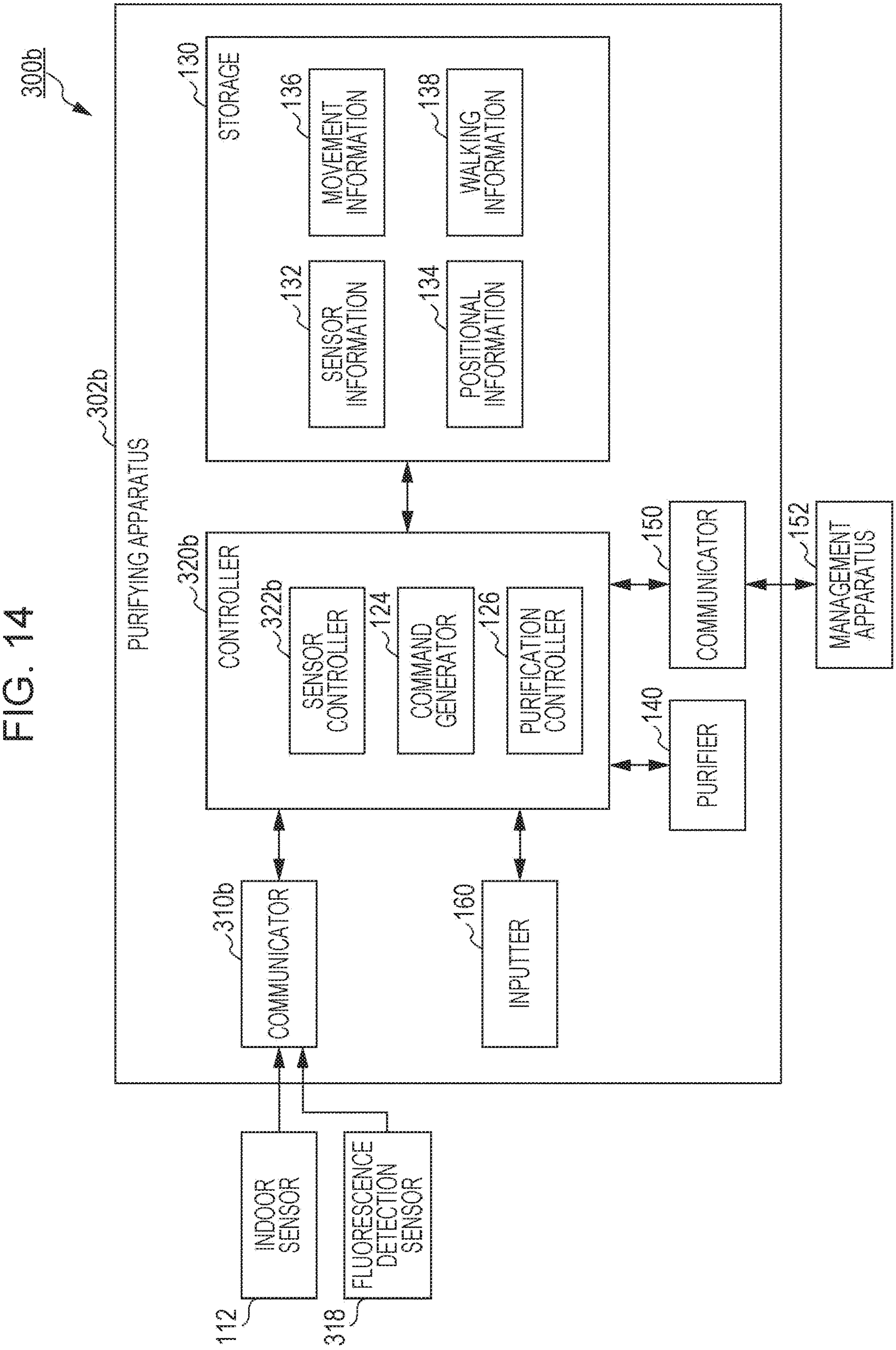
FIG. 14 is a block diagram showing a configuration of a purifying system according to Modification 2 of Embodiment 3.

FIG. 14 is a block diagram showing a configuration of a purifying system 300*b* according to the present modification. As shown in FIG. 14, the purifying system 300*b* differs from the purifying system 300 shown in FIG. 12 in that the purifying system 300*b* includes a purifying apparatus 302*b* and a fluorescence detection sensor 318 instead of the purifying apparatus 302 and the sound sensing sensor 316.

Figure 15:
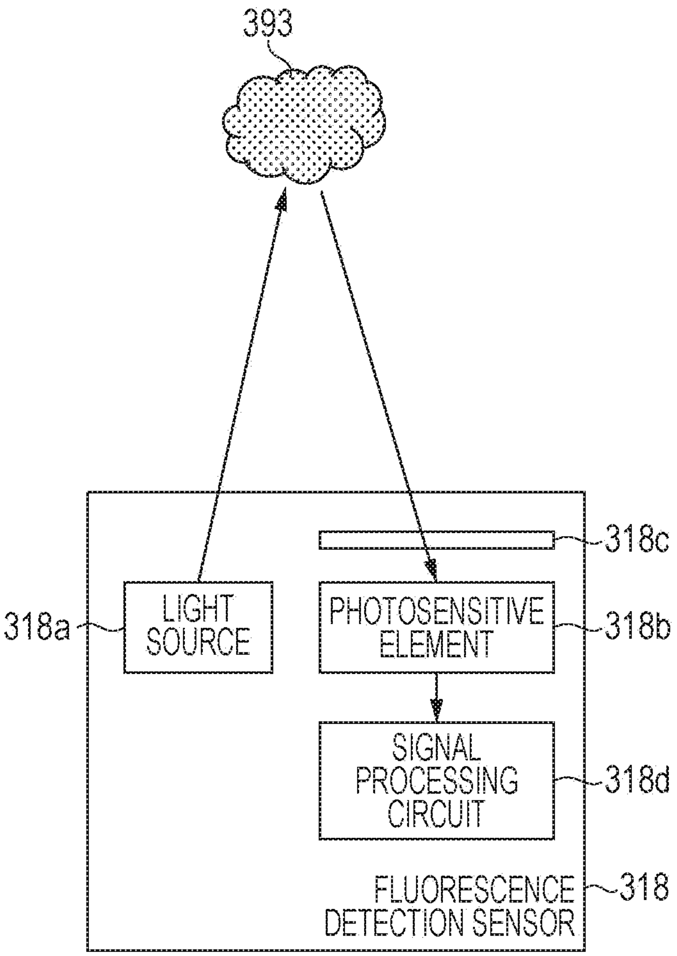
FIG. 15 is a block diagram showing a configuration of a fluorescence detection sensor of the purifying system according to Modification 2 of Embodiment 3.

FIG. 15 is a block diagram showing a configuration of the fluorescence detection sensor 318 of the purifying system 300*b* according to the present modification, FIG. 15 schematically shows an example in which the fluorescence detection sensor 318 detects the aerosol 393. As shown in FIG. 15, the fluorescence detection sensor 318 includes a light source 318*a*, a photosensitive element 318*b*, a spectral element 318*c*, and a signal processing circuit 318*d*.

The light source 318 emits excitation light. The excitation light is light with which a substance to be detected is irradiated so that fluorescence is produced from the substance. The substance to be detected is for example an amino acid that constitutes a bacterium or a virus.

The light source 318*a* is a solid-state light-emitting element such as a semiconductor laser or an LED (light-emitting diode) or a discharge lamp such as a halogen lamp. The light source 318*a* may have a spectral element provided on a light exit side thereof and may emit light of a particular wavelength band as the excitation light. The excitation light has a wavelength falling within, but not limited to, a range of 220 nm to 550 nm. For example, the excitation light is ultraviolet light whose wavelength is not shorter than 250 nm and not longer than 350 nm. The excitation light is pulsed light, but may be continuous light.

The photosensitive element 318*b* receives fluorescence that is produced from a substance upon irradiation of the substance with the excitation light. The photosensitive element 318*b* is for example a photo multiplier tube (PMT) or an avalanche photodiode. The photosensitive element 318*b* may have a photo counter. The photosensitive element 318*b* outputs, to the signal processing circuit 318*d*, an electric signal corresponding to the intensity of the fluorescence thus received. The fluorescence has a wavelength which is longer than that of the excitation light and which falls within, but is not limited to, a range of 250 nm to 1000 nm. For example, the fluorescence is ultraviolet light whose wavelength is not shorter than 270 nm and not longer than 330 nm.

The spectral element 318*c* splits incident light into particular wavelengths. The spectral element 318*c*, provided on a light entrance side of the photosensitive element 318*b*, allows the photosensitive element 318*b* to receive light of a particular wavelength. The particular wavelength is for example a wavelength that is unique to the substance to be detected. For example, in a case where the substance to be detected is an amino acid, the particular wavelength is not shorter than 270 nm and not longer than 330 nm. The spectral element 318*c* is for example a diffraction grating or a bandpass filter. It should be noted that the fluorescence detection sensor 318 does not need to include the spectral element 318*c*.

The signal processing circuit 318*d* processes an electric signal outputted from the photosensitive element 318*b*. The signal processing circuit 318*d* is for example a processor or one or more electronic circuits. The one or more electronic circuits may be general-purpose circuits or may be dedicated circuits.

By processing the electric signal, the signal processing circuit 318*d* detects the amount and position of the substance from which the fluorescence has been produced. Specifically, the signal processing circuit 318*d* detects the amount of the substance on the basis of the intensity of the fluorescence. For example, the signal processing circuit 318*d* has stored in a memory a function or a correspondence table showing a relationship between signal levels of electric signals and amounts of substances. By performing a computation involving the use of the function or referring to the correspondence table, the signal processing circuit 318*d* determines the amount of the substance on the basis of the signal level of the electric signal. The signal level is for example the voltage value or electric current value of the electric signal and is equivalent to the intensity of the fluorescence received by the photosensitive element 318*b*.

Further, the signal processing circuit 318*d* detects the position of the substance by calculating the distance from the fluorescence detection sensor 318 to the substance using the direction in which the excitation light was emitted and the time from the emission of the excitation light to the reception of the fluorescence. The fluorescence detection sensor 318 outputs, as a sensing signal, positional information indicating the position thus detected.

In the present modification, by scanning inside the space 90 while changing the direction of emission of the excitation light from the light source 318*a*, the fluorescence detection sensor 318 can detect organic matter that constitutes bacteria or viruses contained in the aerosol 393 that is present in the space 90. The direction of emission of the excitation light from the light source 318*a* may be a predetermined direction. For example, the fluorescence detection sensor 318 may emit the excitation light toward the door knob 94 and detect organic matter that constitutes bacteria or viruses having adhered to the door knob 94. This makes it possible to perform purification only in a case where bacteria or viruses are adhering to the door knob 94, thus making it possible to effectively utilize the agent.

Further, the fluorescence detection sensor 318 may emit excitation light of a plurality of different wavelengths and receive light of a plurality of different wavelengths. For example, the signal processing circuit 318*d* detects the amount of a substance on the basis of the wavelength of excitation light, a combination of wavelengths of fluorescence received, and the intensity of fluorescence. Specifically, the signal processing circuit 318*d* generates an excitation emission matrix (EEM; so-called fluorescence fingerprints) on the basis of the wavelength of excitation light and the wavelength of light received. Since fluorescence fingerprints are unique to each separate substance, the signal processing circuit 318*d* can identify the type of a substance and detect the amount of bacteria or viruses with a high degree of accuracy.

As is the case with the sound sensing sensor 316 shown in FIG. 12, the fluorescence detection sensor 318 is provided on a wall, a ceiling, or the like that constitutes the space 90.

As is the case with the indoor sensors 112, the fluorescence detection sensor 318 may be integrated with the purifying apparatus 302*b*.

As shown in FIG. 14, the purifying apparatus 302*b* differs from the purifying apparatus 102 according to Embodiment 1 in that the purifying apparatus 302*b* includes a communicator 310*b* and a controller 320*b* instead of the communicator 110 and the controller 120.

The communicator 310*b* performs communication with each of the plurality of indoor sensors 112 and the fluorescence detection sensor 318 by cable or by radio. For example, the communicator 310*b* performs wireless communication conforming to a wireless communication standard such as Wi-Fi (registered trademark), Bluetooth (registered trademark), or ZigBee (registered trademark). The communicator 310*b* acquires sensing signals from each of the plurality of indoor sensors 112 and the fluorescence detection sensor 318. The sensing signals thus acquired are outputted to a sensor controller 322*b* of the controller 320*b*.

As shown in FIG. 14, the controller 320*b* includes the sensor controller 322*b*, a command generator 124, and a purification controller 126. The controller 320*b* is achieved, for example, by a nonvolatile memory in which a program is stored, a volatile memory serving as a transitory recording region in which to execute the program, an liO port, a processor that executes the program, or other components. The sensor controller 322*b*, command generators 124, and purification controller 126 of the controller 320*b* may each be implemented as software that is executed by the processor or may each be implemented as hardware such as an electronic circuit including a plurality of circuit elements.

The sensor controller 322*b* controls operations involving the indoor sensors 112 and the fluorescence detection sensor 318. The operation involving the indoor sensors 112 is the same as that of Embodiment 1. In the present embodiment, the sensor controller 322*b* further determines an intended position on the basis of a sensing signal outputted from the fluorescence detection sensor 318. Specifically, the sensor controller 322*b* acquires, from a sensing signal outputted from the fluorescence detection sensor 318, positional information indicating the position of organic matter and determines, as the intended position, the position indicated by the positional information thus acquired, For example, since the positional information indicates the position of organic matter that constitutes bacteria or viruses contained in the aerosol 393, the sensor controller 322*b* can determine, as the intended positon, a position in which the aerosol 393 is present.

The foregoing configuration allows the purifying system 300*b* according to the present modification to efficiently remove bacteria or viruses coughed or sneezed into the space 90 and floating in the space 90, By sensing fluorescence emitted by organic matter that constitutes bacteria or viruses, the position of the organic matter can be detected with a high degree of accuracy, so that the bacteria or the viruses can be efficiently removed.

The operation of the purifying system 300*b* according to the present modification is the same as the operation of the purifying system 100 according to Embodiment 1. In this case, the operation shown in FIG. 6 may be started upon detection of fluorescence by the fluorescence detection sensor 318. For example, the command generator 124 may generate a purification command upon sensing of fluorescence by the fluorescence detection sensor 318.

The purifying system 300*b* according to the present modification may include only the light source 318*a* instead of the fluorescence detection sensor 318. The light source 318*a* is for example a black light that emits ultraviolet radiation. A user may input, to the inputter 160, a position in which fluorescence has been emitted in a case where the light source 318*a* has been turned on.

Embodiment 4

Next, Embodiment 4 is described.

Embodiments 1 to 3 have illustrated an example in which ejected matter is a vortex ring formed from a gas containing the agent. On the other hand, Embodiment 4 illustrates an example in which ejected matter does not contain an agent. It should be noted that the following gives a description with a focus on differences from Embodiments 1 to 3 and omits or simplifies a description of common features.

Figure 16:
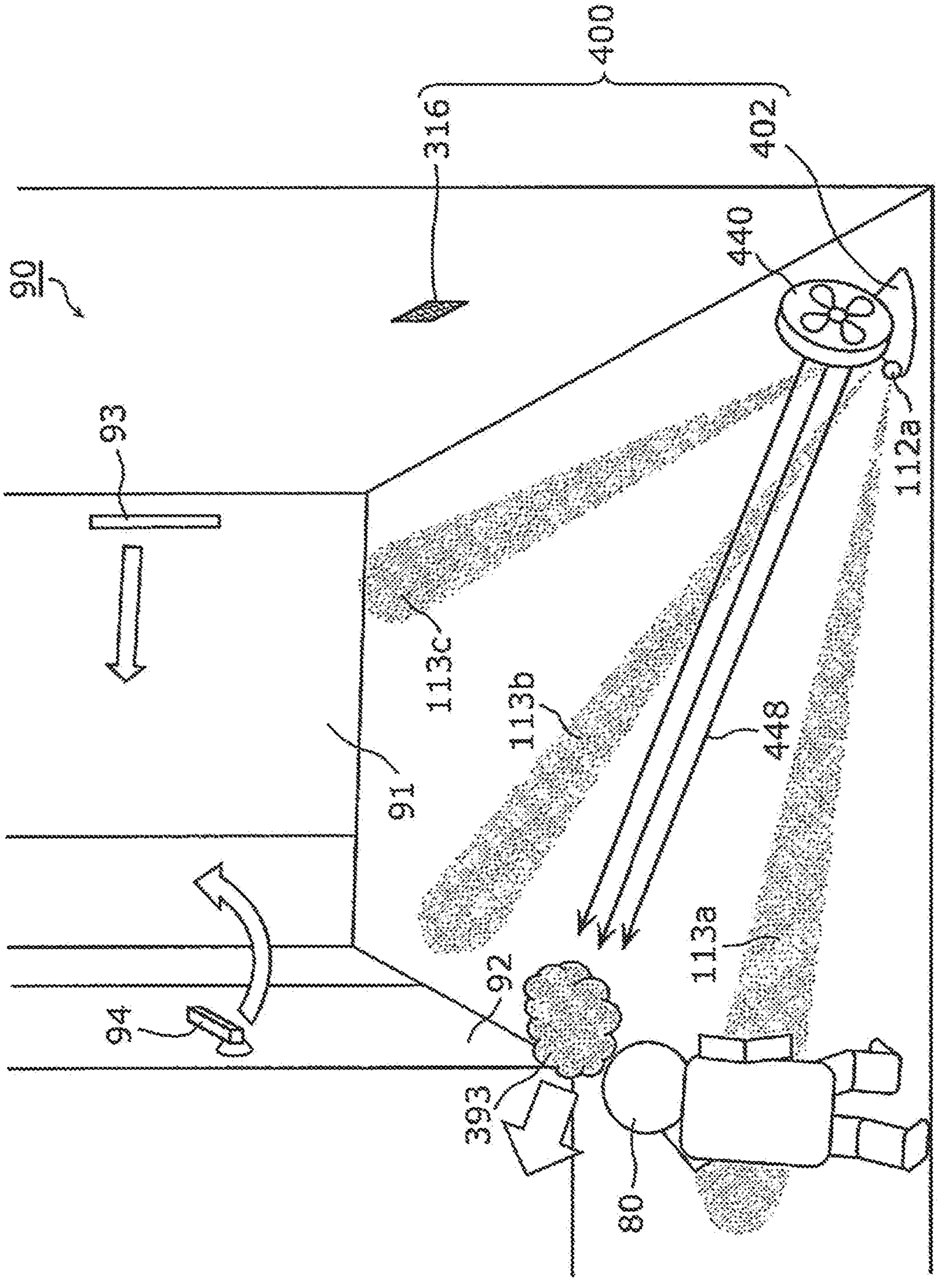
FIG. 16 is a diagram presenting an overview of a purifying system according to Embodiment 4.

FIG. 16 is a diagram presenting an overview of a purifying system 400 according to the present embodiment. FIG. 16 schematically shows an aerosol 393 floating in the space 90. As in the case of Embodiment 3, the aerosol 393 is viruses or bacteria, pollen, or the like.

Figure 17:
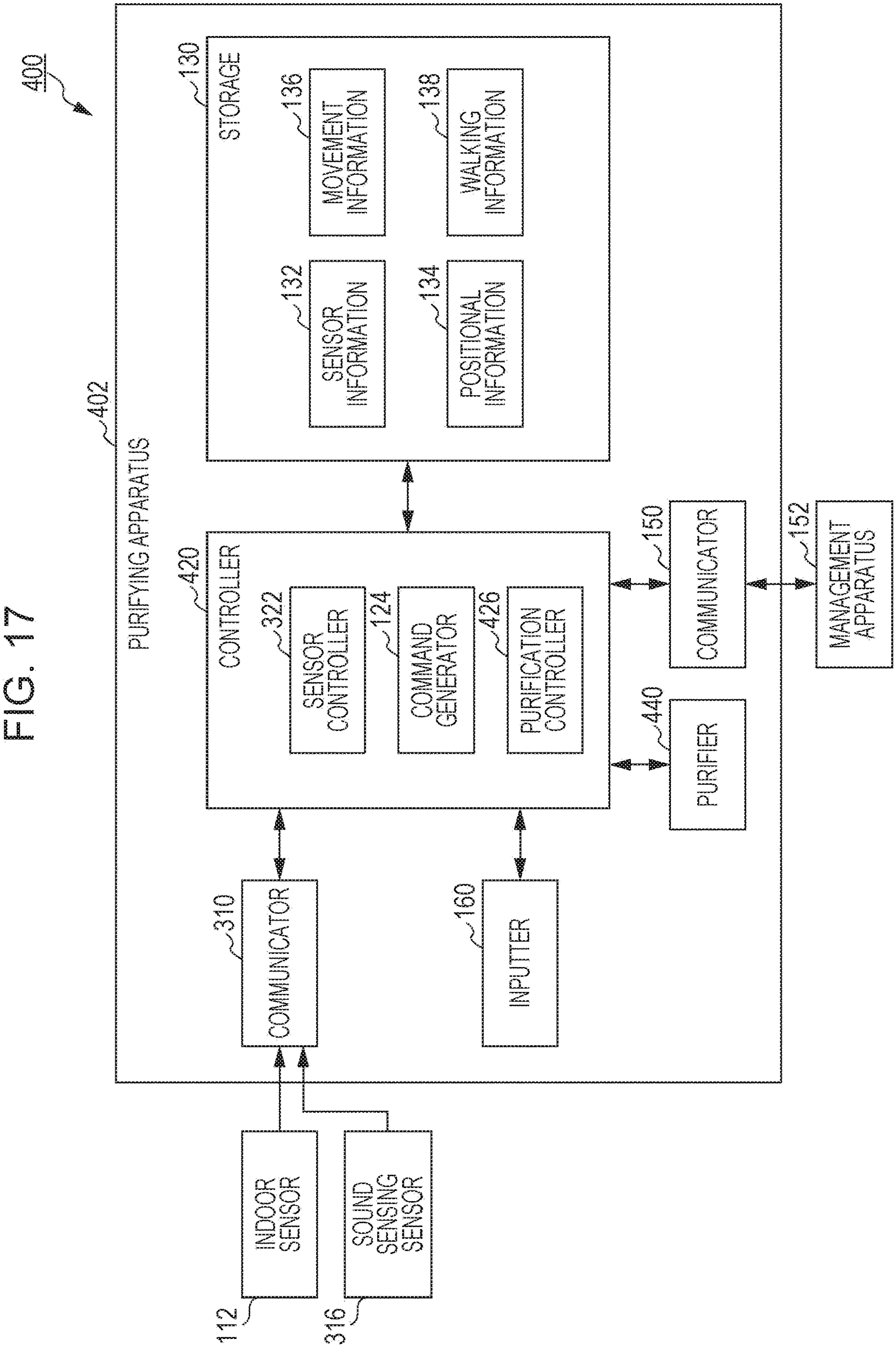
FIG. 17 is a block diagram showing a configuration of the purifying system according to Embodiment 4.

FIG. 17 is a block diagram showing a configuration of the purifying system 400 according to the present embodiment. As shown in FIG. 17, the purifying system 400 differs from the purifying system 300 according to Embodiment 3 in that the purifying system 400 includes a purifying apparatus 402 instead of the purifying apparatus 302. The purifying apparatus 402 includes a controller 420 and a purifier 440 instead of the controller 320 and the purifier 140. The purifying system 400 may include at least either an imaging element 317 or a fluorescence detection sensor 318 instead of or in addition to the sound sensing sensor 316.

As shown in FIG. 17, the controller 420 includes a sensor controller 322, a command generator 124, and a purification controller 426. The controller 420 is achieved, for example, by a nonvolatile memory in which a program is stored, a volatile memory serving as a transitory recording region in which to execute the program, an I/O port, a processor that executes the program, or other components. The sensor controller 322, command generators 124, and purification controller 426 of the controller 420 may each be implemented as software that is executed by the processor or may each be implemented as hardware such as an electronic circuit including a plurality of circuit elements.

The purification controller 426 controls the purifier 440. Specifically, the purification controller 426 judges, on the basis of an intended position determined by the sensor controller 322, whether the person 80 touches ejected matter within a period of time from ejection of the ejected matter from the purifier 440 to reaching of the ejected matter to the intended position. The purification controller 426 controls, on the basis of a result of the judgment, how the purifier 440 ejects the ejected matter into an area including the intended position. A specific process for judgment is the same as that of Embodiment 1.

In the present embodiment, control parameters for setting the content of control of the purifier 440 are different from those of Embodiments 1 to 3. Specifically, since the purifier 440 generates an air current 448, the control parameters include at least one of the wind direction, velocity, and air volume of the air current and an air-sending period. The direction of the air current is for example a direction in which the air current passes through the intended position and does not impinge on the person 80.

The purifier 440 is an example of an ejector that ejects ejected matter. Specifically, as shown in FIG. 16, the purifier 440 ejects the air current 448 as ejected matter. In the present embodiment, the air current 448 does not contain an agent, The purifier 440 is for example an air-sending mechanism such as a fan. The purifier 440 does not include a tank in which to store an agent.

Ejected matter that is ejected by the purifier 440 may be a liquid or a mist, In this case, the liquid or the mist does not need to contain an agent. For example, the liquid or the mist may be water such as tap water. By applying the liquid to the door knob 94, the purifier 440 can wash away organic matter or the like from the door knob 94. Alternatively, for example, by ejecting the mist into the space 90, the purifier 440 can cause microparticles of a liquid constituting the mist to take in the aerosol 393 and fall onto a floor surface.

The foregoing configuration allows the purifying system 400 according to the present embodiment to efficiently purify an intended position even without the use of an agent. Specifically, as indicated by the arrow outline with a blank inside drawn in the vicinity of the aerosol 393 in FIG. 16, the concentration of bacteria or viruses in the space 90 can be reduced by causing the aerosol 393 to be moved or dissipated by the air current 448. Further, the air current 448 may be released toward the door knob 94 as well as the aerosol 393. This makes it possible to blow dirty substances or the like off of the door knob 94 with the air current 448.

Thus, in the present embodiment, the term "purification" not only means decomposing bacteria or viruses into disappearance but also means reducing the concentration of bacteria or viruses by moving or dissipating them. For example, the concentration of bacteria or viruses in an intended position in the space 90 can be reduced by moving them to a window, a vent, an overflow, or the like provided in the space 90. Accordingly, the purifying system 400 according to the present embodiment makes it possible to efficiently purify an intended position even without the use of an agent.

Other Embodiments

In the foregoing, purifying apparatuses, purifying systems, and purifying methods according to one or more aspects have been described with reference to embodiments; however, the present disclosure is not intended to be limited to these embodiments. Applications to the present embodiments of various types of modification conceived of by persons skilled in the art and embodiments constructed by combining constituent elements of different embodiments are encompassed in the scope of the present disclosure, provided such applications and embodiments do not depart from the spirit of the present disclosure.

For example, although each of the embodiments has described, as an example of a restriction that is imposed on the ejection in a case where it is judged that the person 80 touches the ejected matter, an example in which the ejection is waited or canceled, this is not intended to impose any limitation. For example, the purifying apparatus may change conditions for the ejection of the ejected matter. Specifically, the purifying apparatus increases the speed of ejection of the ejected matter or shortens the duration of ejection. This allows the ejected matter to reach the intended position before the person 80 enters the path of travel of the ejected matter. The speed of ejection or the duration of ejection is determined on the basis of the time it takes for the person 80 to touch the ejected matter in a case where it has been judged that the person 80 touches the ejected matter.

Further, for example, in a case of where the ejection is waited, the ejected matter may be ejected after a waiting time has been calculated on the basis of the moving speed of the person 80 and the waiting time thus calculated has elapsed. In this case, it is not necessary to, after the waiting time has elapsed, judge whether the person 80 touches the ejected matter.

Further, for example, although, in Embodiment 1 or 2, the purifying apparatus 102 or 202 ejects the agent by ejecting a vortex ring 148 containing the agent, the method for ejecting the agent is not limited to the utilization of a vortex ring 148. For example, the purifying apparatus 102 or 202 may have a nozzle through which a misty or gaseous agent is sprayed. Alternatively, the purifying apparatus 102 or 202 may convey a microparticulated agent by an ultrasonic-assisted conveying technique.

Further, for example, although Embodiment 2 has illustrated an example in which the purifying system 200 includes the indoor sensors 112 and the outdoor sensors 214, the purifying system 200 does not need to include the indoor sensors 112 and may include only the outdoor sensors 214.

Further, for example, in each of the embodiments, the purifying system does not need to include the management apparatus 152, Further, for example, the purifying apparatus according to each of the embodiments may include at least one of an indoor sensor 112, a sound sensing sensor 316, an imaging element 317, and a fluorescence detection sensor 318. Further, for example, the purifying apparatus according to each of the embodiments may include both a purifier 140 and a purifier 440.

Further, the method for communication between apparatuses described in each of the embodiments is not limited to a particular method. In a case where wireless communication is performed between apparatuses, the scheme for wireless communication (communication standard) is for example Near Field Communication such as ZigBee (registered trademark), Bluetooth (registered trademark), or a wireless LAN (local area network). Alternatively, the scheme for wireless communication (communication standard) may be communication via a wide area communication network such as the Internet. Further, cable communication may be performed instead of wireless communication between apparatuses. A specific example of cable communication is power line communication (PLC) or communication involving the use of a wired LAN.

Further, in each of the embodiments, a process that is executed by a particular processor may be executed by another processor. Further, the order of a plurality of processes may be changed, or a plurality of processes may be executed in parallel. Further, the assignment of the constituent elements of the purifying system to the plurality of apparatuses is a mere example. For example, one apparatus may include the constituent elements of another apparatus. Further, the purifying system may be implemented as a single apparatus.

For example, a process described in each of the embodiments may be realized by centralized processing using a single apparatus (system) or may be realized by decentralized processing using a plurality of apparatuses. Further, the program may be executed by a single processor or a plurality of processors. That is, centralized processing may be performed, or decentralized processing may be performed.

Further, in each of the embodiments described above, all or some of the constituent elements such as the controller may be configured by dedicated hardware or may be realized by executing a software program suited to that constituent element. Each of the constituent elements may be realized by a program executor such as a CPU (central processing unit) or a processor reading and executing a software program stored on a storage medium such as an HDD (hard disk drive) or a semiconductor memory.

Further, a constituent element such as the controller may be constituted by one or more electronic circuits. The one or more electronic circuits may each be a general-purpose circuit or may each be a dedicated circuit.

The one or more electronic circuits may include, for example, a semiconductor device, an IC (integrated circuit), an LSI (large-scale integrated circuit), or the like. The LSI or IC can be integrated into one chip, or also can be integrated into a plurality of chips. The name used here is LSI or IC, but it may also be called system LSI, VLSI (very large scale integration), or ULSI (ultra large scale integration) depending on the degree of integration. A Field Programmable Gate Array (FPGA) that can be programmed after manufacturing an LSI can be used for the same purpose.

It should be noted that general or specific embodiments may be implemented as a system, an apparatus, a method, an integrated circuit, or a computer program. Alternatively, general or specific embodiments may be implemented as a computer-readable non-transitory storage medium, such as an optical disk, an HDD, a semiconductor memory, having the computer program stored thereon, It should be noted that general or specific embodiments may be implemented as any selective combination of a system, an apparatus, a method, an integrated circuit, a computer program, and a storage medium.

Further, each of the embodiments described above is subject to various changes, substitutions, additions, omissions, and the like in the scope of the claims or the scope of equivalents thereof.

What is claimed is:

1. A purifying method comprising:

determining an intended position that ejected matter ejected from a purifier is made to reach, the purifier including an ejection port;

judging whether an object touches the ejected matter within a period of time from ejection of the ejected matter from the purifier to reaching of the ejected matter to the intended position based on positional information on the object, wherein the object is at a resting state or a moving state, and the positional information is obtained by a first sensor; and controlling, based on a result of the judging, how the purifier ejects the ejected matter into an area including the intended position, wherein:

in a case where it has been judged in the judging that the object does not touch the ejected matter, in the controlling, the purifier is made to eject the ejected matter into the area, and in a case where it has been judged in the judging that the object touches the ejected matter, in the controlling, the purifier is restricted from ejecting the ejected matter into the area so that the ejected matter does not touch the object.

2. The purifying method according to claim 1, wherein the ejected matter contains an agent.

3. The purifying method according to claim 1, wherein in the determining, the intended position is determined by using a second sensor.

4. The purifying method according to claim 3, wherein the second sensor is at least one selected from the group consisting of a sound sensing sensor, an infrared sensor, an imaging element, and a fluorescence detection sensor.

5. The purifying method according to claim 3, wherein an aerosol is present in the intended position, and the intended position is in a space where the purifier is disposed.

6. The purifying method according to claim 1, wherein in the determining, a predetermined position is determined as the intended position.

7. The purifying method according to claim 1, wherein the intended position is at least a part of a door disposed in a space in which the purifier is disposed.

8. The purifying method according to claim 1, wherein the first sensor is disposed in a second space separated by a door from a first space in which the purifier is disposed, the purifying method further comprising:

judging, based on the positional information on the object, whether the object approaches the door within the period of time; and in a case where it has been judged that the object approaches the door, restricting the purifier from ejecting the ejected matter.

9. The purifying method according to claim 1, wherein the controlling includes waiting ejection of the ejected matter for a first period of time or canceling ejection of the ejected matter.

10. The purifying method according to claim 1, further comprising:

judging whether a state of the object is the resting state or the moving state;

in a case where it has been judged that the state of the object is the resting state, judging whether the resting state has been continuing for a second period of time or longer; and in a case where it has been judged that the resting state has been continuing for the second period of time or longer, outputting a signal for making a warning sound or a warning display.

11. The purifying method according to claim 1, wherein the ejected matter is an air current or a mist.

12. The purifying method according to claim 11, wherein the ejected matter is the air current, and the air current includes a vortex ring formed by a gas containing an agent.

* * * * *